United States Patent
Sachs et al.

(10) Patent No.: US 7,125,847 B1
(45) Date of Patent: Oct. 24, 2006

(54) MECHANICALLY ACTIVATED CHANNEL BLOCKER

(75) Inventors: Frederick Sachs, Eden, NY (US); Thomas Suchyna, Amherst, NY (US); Janice Johnson, Salt Lake City, UT (US)

(73) Assignee: The Research Foundation of State University of New York at Buffalo, Amherst, NY (US)

( * ) Notice: Subject to any disclaimer, the term of this patent is extended or adjusted under 35 U.S.C. 154(b) by 348 days.

(21) Appl. No.: 10/397,595

(22) Filed: Mar. 26, 2003

Related U.S. Application Data

(63) Continuation-in-part of application No. 09/827,814, filed on Apr. 6, 2001, now abandoned.

(60) Provisional application No. 60/405,385, filed on Aug. 23, 2002, provisional application No. 60/277,071, filed on Mar. 19, 2001, provisional application No. 60/195,528, filed on Apr. 7, 2000.

(51) Int. Cl.
*A61K 38/00* (2006.01)
*A61K 38/16* (2006.01)
*C07K 14/00* (2006.01)
*C07K 1/00* (2006.01)

(52) U.S. Cl. ........................ 514/12; 530/300; 530/324; 514/2

(58) Field of Classification Search ...................... None
See application file for complete search history.

(56) References Cited

U.S. PATENT DOCUMENTS

| 4,925,664 | A | 5/1990 | Jackson et al. |
| 5,756,663 | A | 5/1998 | Lampe et al. |
| 5,968,838 | A | 10/1999 | Lampe et al. |

OTHER PUBLICATIONS

Suchyna et al. Identification of a Peptide Toxin from *Grammastola spatulata* Spider Venom that Blocks Cation-Selective Stretch-activated Channels. May 2000, J. Gen. Physiol. vol. 115, pp. 583-598.*
Craik et al. The cystine knot motif in toxins and implications for drug design. 2001, Toxicon, vol. 39, pp. 43-60.*
Nazir et al., *Effects of G. spatulata Venom, a Novel Stretch-Activated Channel Blocker in a Model of Stretch-Induced Ventricular Fibrillation in the Isolated Heart*, Abstracts from the 68th Scientific Sessions, Oct. 15, 1995, vol. 2 (Suppl. I), p. 641.

* cited by examiner

*Primary Examiner*—Nashaat T. Nashed
*Assistant Examiner*—Holly Schnizer
(74) *Attorney, Agent, or Firm*—Hodgson Russ LLP

(57) ABSTRACT

The present invention discloses a peptide of SEQ ID NO:2 and its variants that blocks stretch-activated ion channels. The peptide, designated as GsMTx-4, is present in the venom of the spider *Grammostola spatulata*. The present invention also discloses a method of purifying the peptide GsMTx-4 from the spider venom and a method for inhibition of stretch activated ion channels in a cell. The cDNA sequence encoding the GsMTx-4 is also disclosed. This peptide and its variants can be used for the treatment of cardiac arrhythmias.

14 Claims, 24 Drawing Sheets

```
GsMTx-4        G C L E - F W W K C N P N D D K C C R P K L K C S K L F K L - - C N F S S G -amide
TXP5           S   V D - Q T   K K D S   -   - G   E   S R W W - - V Y P   P F
SNX-482  G V D K R Y M   G G -   S V     -   - R   G   H S     S Y - - A W D L T F S D
ω-GsTx-S1A     D   R -     G     S Q T S -   -     A   K S K   P R N I V   D G S V
Hanatoxin₁     E   R Y L   G G -   K T T S -   -   G   K F R D   Y - - A W D F T K S
```

Figure 2

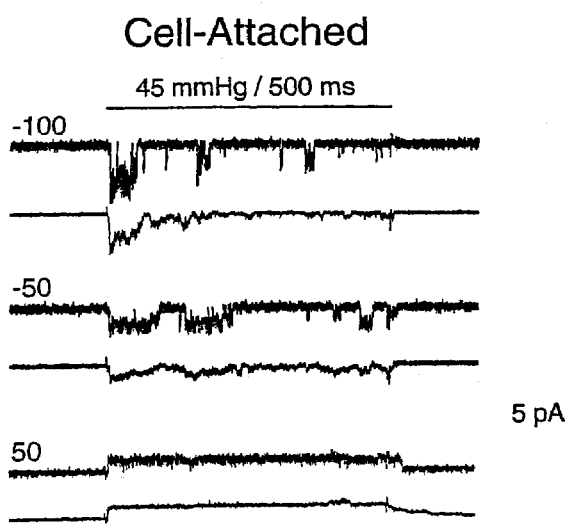
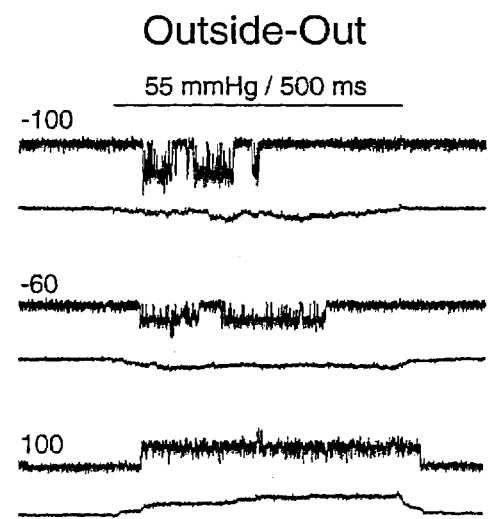
Figure 3A                     Figure 3B

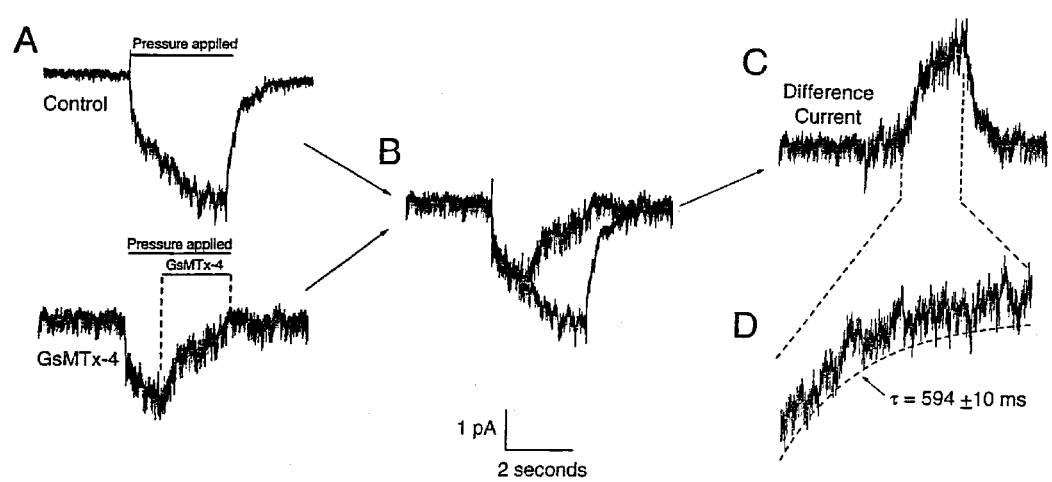
Figure 5 A-D

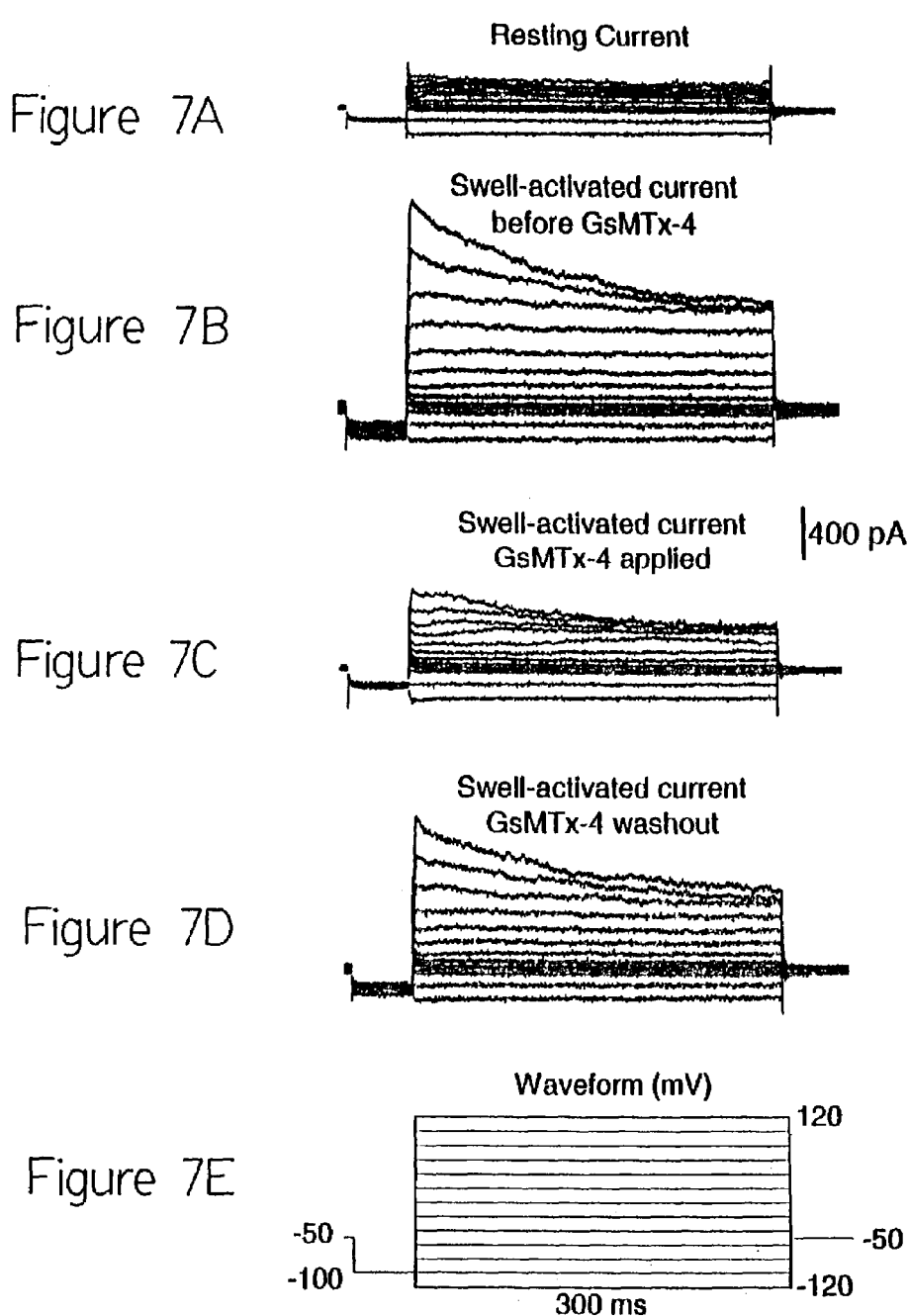

ATG AAG ACA TCT GTG GTG TTC GTC ATT GCA GGC TTA GCT CTG CTT TCA GTT GTC
M   K   T   S   V   V   F   V   I   A   G   L   A   L   L   S   V   V

TGT TAT GCT TCA GAA CTG AAG GAG CAA AGT TCC GTC AAT GAA GTG CTT TCT ACA
C   Y   A   S   E   L   K   E   Q   S   S   V   N   E   V   L   S   T

ATT TTT CAT TTT GAA CAA CCT GAG GAA AGA GGC TGT TTG GAA TTT TGG TGG AAA
I   F   H   F   E   Q   P   E   E   R   G   C   L   E   F   W   W   K

TGC AAC CCT AAC GAC GAC AAA TGC TGT CGT CCA AAA TTG AAA TGC AGT AAA CTG
C   N   P   N   D   D   K   C   C   R   P   K   L   K   C   S   K   L

TTC AAG TTG TGT AAC TTT TCA TTC GGC AAG TAA
F   K   L   C   N   F   S   F   G   K   Stop

Figure 11

SEQUENCE LISTING

```
<160> NUMBER OF SEQ ID NOS: 18

<210> SEQ ID NO 1
<211> LENGTH: 35
<212> TYPE: PRT
<213> ORGANISM: Grammastola spatulata

<400> SEQUENCE: 1

Gly Cys Leu Glu Phe Trp Trp Lys Cys Asn Pro Asn Asp Asp Lys
                 5                  10                  15

Cys Cys Arg Pro Lys Leu Lys Cys Ser Lys Leu Phe Lys Leu Cys
                20                  25                  30

Asn Phe Ser Ser Gly
                35

<210> SEQ ID NO 2
<211> LENGTH: 36
<212> TYPE: PRT
<213> ORGANISM: Grammastola spatulata

<400> SEQUENCE: 2

Gly Cys Leu Glu Phe Trp Trp Lys Cys Asn Pro Asn Asp Asp Lys
                 5                  10                  15

Cys Cys Arg Pro Lys Leu Lys Cys Ser Lys Leu Phe Lys Leu Cys
                20                  25                  30

Asn Phe Ser Phe Gly Lys
                35

<210> SEQ ID NO 3
<211> LENGTH: 34
<212> TYPE: PRT
<213> ORGANISM: Grammastola spatulata

<400> SEQUENCE: 3

Gly Cys Leu Glu Phe Trp Trp Lys Cys Asn Pro Asn Asp Asp Lys
                 5                  10                  15
```

```
Cys Cys Arg Pro Lys Leu Lys Cys Ser Lys Leu Phe Lys Leu Cys
         20                  25                  30

Asn Phe Ser Phe

<210> SEQ ID NO 4
<211> LENGTH: 249
<212> TYPE: DNA
<213> ORGANISM: Grammastola spatulata

<400> SEQUENCE: 4
atgaagacat ctgtggtgtt cgtcattgca ggcttagctc tgctttcagt         50
tgtctgttat gcttcagaac tgaaggagca aagttccgtc aatgaagtgc        100
tttctacaat ttttcatttt gaacaacctg aggaaagagg ctgtttggaa        150
ttttggtgga aatgcaaccc taacgacgac aaatgctgtc gtccaaaatt        200
gaaatgcagt aaactgttca agttgtgtaa cttttcattc ggcaagtaa         249

<210> SEQ ID NO 5
<211> LENGTH: 24
<212> TYPE: DNA
<213> ORGANISM: Artificial sequence
<220> FEATURE:
<223> OTHER INFORMATION: 5' RACE MTx 4-1 primer

<400> SEQUENCE: 5
tcgttggggt tgcacttcca ccag                                    24

<210> SEQ ID NO 6
<211> LENGTH: 25
<212> TYPE: DNA
<213> ORGANISM: Artificial sequence
<220> FEATURE:
<223> OTHER INFORMATION: 3' RACE MTx 4-1 primer

<400> SEQUENCE: 6
ttctggtgga agtgcaaccc caacg                                   25

<210> SEQ ID NO 7
<211> LENGTH: 24
<212> TYPE: DNA
<213> ORGANISM: Artificial sequence
<220> FEATURE:
<223> OTHER INFORMATION: 5' RACE MTx 4-2 primer

<400> SEQUENCE: 7
gccattgttt ccagttctag atca                                    24

<210> SEQ ID NO 8
<211> LENGTH: 27
<212> TYPE: DNA
<213> ORGANISM: Artificial sequence
<220> FEATURE:
<223> OTHER INFORMATION: 3' RACE MTx 4-2 primer

<400> SEQUENCE: 8
cgacaatgaa gacatctgtg gtgttcg                                 27

<210> SEQ ID NO 9
<211> LENGTH: 28
<212> TYPE: DNA
<213> ORGANISM: Artificial sequence
<220> FEATURE:
<223> OTHER INFORMATION: TA-MTx4-1 forward primer
```

```
<400> SEQUENCE: 9
tctgcagaat ctcggttagt tgttgttt                                          28

<210> SEQ ID NO 10
<211> LENGTH: 27
<212> TYPE: DNA
<213> ORGANISM: Artificial sequence
<220> FEATURE:
<223> OTHER INFORMATION: TA-MTx4-1 reverse primer

<400> SEQUENCE: 10
tcgagaagtt tggatctcca cgtatcc                                           27

<210> SEQ ID NO 11
<211> LENGTH: 28
<212> TYPE: DNA
<213> ORGANISM: Artificial sequence
<220> FEATURE:
<223> OTHER INFORMATION: TA-MTx4-2 forward primer

<400> SEQUENCE: 11
atgaagacat ctgtggtgtt cgtcattg                                          28

<210> SEQ ID NO 12
<211> LENGTH: 28
<212> TYPE: DNA
<213> ORGANISM: Artificial sequence
<220> FEATURE:
<223> OTHER INFORMATION: TA-MTx4-2 reverse primer

<400> SEQUENCE: 12
ttacttgccg aatgaaaagt tacacaac                                          28

<210> SEQ ID NO 13
<211> LENGTH: 45
<212> TYPE: DNA
<213> ORGANISM: Artificial sequence
<220> FEATURE:
<223> OTHER INFORMATION: Forward PCR primer

<400> SEQUENCE: 13
gcacgtggta ccctggtgcc acgcggctct atgggctgcc tggaa                       45

<210> SEQ ID NO 14
<211> LENGTH: 27
<212> TYPE: DNA
<213> ORGANISM: Artificial sequence
<220> FEATURE:
<223> OTHER INFORMATION: Reverse PCR primer

<400> SEQUENCE: 14
gcacgctcga gctacgcgct gctaaag                                           27

<210> SEQ ID NO 15
<211> LENGTH: 31
<212> TYPE: DNA
<213> ORGANISM: Artificial sequence
<220> FEATURE:
<223> OTHER INFORMATION: Forward primer

<400> SEQUENCE: 15
ctgtgcaact ttagcttcgc gtagctcgag c                                      31

<210> SEQ ID NO 16
```

-continued

```
<211> LENGTH: 31
<212> TYPE: DNA
<213> ORGANISM: Artificial sequence
<220> FEATURE:
<223> OTHER INFORMATION: Reverse primer

<400> SEQUENCE: 16
gctcgagcta cgcgaagcta aagttgcaca g                              31

<210> SEQ ID NO 17
<211> LENGTH: 33
<212> TYPE: DNA
<213> ORGANISM: Artificial sequence
<220> FEATURE:
<223> OTHER INFORMATION: Forward primer

<400> SEQUENCE: 17
gcaactttag cttctagtag ctcgagcacc acc                            33

<210> SEQ ID NO 18
<211> LENGTH: 33
<212> TYPE: DNA
<213> ORGANISM: Artificial sequence
<220> FEATURE:
<223> OTHER INFORMATION: Reverse primer

<400> SEQUENCE: 18
cgttgaaatc gaagatcatc gagctcgtgg tgg                            33
```

MECHANICALLY ACTIVATED CHANNEL BLOCKER

This application claims priority to U.S. provisional application No. 60/405,385 filed on Aug. 23, 2002 and is also a continuation-in-part of U.S. application Ser. No. 09/827,814 filed on Apr. 6, 2001, now abandoned which claims priority to U.S. provisional application No. 60/195,528 filed on Apr. 7, 2000 and U.S. provisional application No. 60/277,071 filed on Mar. 19, 2001, the disclosures of which are incorporated herein by reference.

FIELD OF THE INVENTION

The present invention relates to the field of stretch-activated channels. More particularly the present invention provides peptides that blocks stretch-activated channels, such as those associated with cardiac arrhythmias.

DISCUSSION OF RELATED ART

Cardiac fibrillation is a frequent cause of sudden death. Atrial fibrillation is the most common sustained cardiac arrhythmia to occur in humans, second only to valve disease, hypertension, or heart failure. Atrial fibrillation is often associated with passive stretching of the arterial chamber arising from haemodynamic or mechanical dysfunction of the heart. It has been suggested that abnormal mechanical factors induce electrophysical changes conducive to arrhythmia via "mechanoelectric feedback". Stretch-activated channels (SACs) have been postulated as a mechanism of mechanoelectric feedback and they may play a role in the genesis of cardiac arrhythymias.

Mechanosensitive ion channels (MSCs), of which SACs are an example, were discovered in tissue cultured skeletal muscle cells using single channel patch clamp recordings. They have since been found in both the plant and animal kingdoms and in the cells of most tissues, including myocardial tissue. Most of them open with increasing membrane tension (stretch-activated channels (SACs)), but a few are tonically active and close with increasing tension (stretch-inactivated channels (SICs)). It is now well recognized that myocardial stretch can cause arrhythmias due to stretch-induced depolarizations.

Ion selectivity of the MSC channel family is variable, as in the case of voltage-activated or ligand-activated channel families. In the animal cells, the most common forms are cation selective and, more particularly, potassium selective. The cation channels will pass divalents such as $Ca^{+2}$ and $Ba^{+2}$ as well as monovalents. Due to their ability to pass $Ca^{+2}$, effects of cationic MSCs are potentially complicated. Even under voltage clamp conditions, incoming $Ca^{+2}$ may activate other channels, such as $Ca^{2+}$ activated $Cl^-$ channels, a link that has been invoked in the regulation of cell volume.

SACs have been implicated as either activators or modifiers of many different cellular responses to mechanical stimuli including modification of electrical and contractile activity of muscle tissue. Consequently, SACs have been implicated in mechanical sensitivity of the heart. Mechanical stimulation of cardiac myocytes and whole heart preparations can cause depolarization, extrasystoles and arrhythmias (Hu et al., 1997; *J Mol Cell Cardiol* 29:1511–1523). Also, chronic hemodynamic stress that leads to congestive heart failure (CHF) and the accompanying cellular hypertrophy may be initiated by stretch- or swelling-activated currents (Sachs, 1988; *Crit Rev Biomed Eng* 16:141–169; Vandenberg et al., 1996; *Cardiovasc Res* 32:85–97; Clemo et al., 1997; *J Gen Physiol* 110:297–312).

SACs are the only major class of ion channels for which a specific inhibitor is not known. $Gd^{3+}$ is the best known blocker of SACs ($K_D$'s ranging from 1–100 mM) and is widely used to identify these channels. However, $Gd^{3+}$ also blocks a variety of other channels such as L- and T-type $Ca^{2+}$ (Biagi et al., 1990, *Am. J. Physiol.*, 264:C1037–1044), $K^+$ delayed rectifier, voltage-gated $Na^+$ (Elinder et al., 1994, *Biophys. J*, 67:71–83) and $Ca^{2+}$ ER release channels (Kluesener et al., 1995, *EMBO J.*, 14:2708–2714). A variety of blockers for voltage- and ligand-gated channels (e.g. amiloride, cationic antibiotics, tetrodotoxin, tetraethylammonium, quinidine, diltiazem and verapamil) exhibit low affinity blocking activity against SACs (for review see Hamill et al., 1996, *Pharmacol Rev* 48:231–252; Sachs et al., 1998; M. P. Blaustein, R. Greger, H. Grunicke, r. Jalm, L. M. Mendell, A. Miyajima, D. Pette, G. Schultz, and M. Schwieger, editors; Springer, Berlin 1–78).

Thus, while several studies point to a role for SACs in mechanical sensitivity, a lack of specific SAC agent has hampered the development of SAC based approach to the treatment of arrhythmias. Consequently, there is an ongoing need to identify agents that can block SACs. Such agents could be useful in influencing events associated with cardiac arrhythmias, and could be the first of a new class of anitarrhythmic agents to be directed against the causes rather than the symptoms of fibrillation.

SUMMARY OF THE INVENTION

The present invention discloses a peptide a peptide present in the in the venom of the spider *Grammostola spatulata*. This peptide blocks stretch-activated ion channels. The peptide is designated as GsMTx-4. The amino acid sequence of this peptide is disclosed in SEQ ID NO:2. Variants of this peptide having stretch activated channel blocking activity are also disclosed.

The present invention also discloses a method of purifying the peptide GsMTx-4 from the spider venom. The method comprises the steps of multiple fractionations of the spider venom.

The present invention also provides a method for inhibition of stretch activated ion channels in a cell. The method comprises the step of applying to the cell a sufficient amount of the peptide GsMTx-4.

The present invention also provides a method for the treatment of cardiac arrhythmias. The method comprises the step of applying the peptide GsMTx-4 to a heart tissue that is exhibiting arrhythmia.

The present invention also discloses a method for identifying the presence of the peptide GsMTx-4 in venom. The method comprises the steps of fractionating the venom sample, and assaying the effect of the fractions on SAC activity using patch clamp recordings.

The present invention also provides a cDNA sequence (SEQ ID NO:4) encoding GsMTx4. The gene is translated as a preproprotein of 80 amino acids. The first 21 amino acids are a predicted signal sequence and the C-terminal residues are a signal for amidation. An arginine residue adjacent to the N-terminal glycine of GsMTx4 is the cleavage site for release. The resulting peptide is 34 amino acids in length with a C-terminal phenylalanine. In one embodiment, the peptide was chemically synthesized. This peptide folded in 0.1M Tris, pH 7.9 with oxidized/reduced glutathione (1/10). Properties of the synthetic peptide were identical to the wild type for HPLC, mass spectrometry, CD, and NMR. In another embodiment, GsMTx4 was cloned in a thioredoxin fusion protein system containing 6 histidines. Nickel affinity columns allowed rapid purification and folding occurred in conditions described above with 0.5M guanidiniumHCl present. Thrombin cleavage liberated GsMTx4 with three extra amino acids at the N-terminus. The retention time in HPLC analysis and the CD spectrum was similar to wild type. Both the synthetic and cloned peptides were active in blocking SACs.

BRIEF DESCRIPTION OF THE DRAWINGS

FIG. 2 is a representation of the sequence of GsMTx-4 variant showing homology to other ion channel peptide toxins. Cysteine motif residues are included in boxes. Dark shaded residues in the comparison peptide sequences are identical to GsMTx-4 variant, while lighter shaded residues are similar.

FIGS. 3A–3D are representations of cell-attached and outside-out patches from adult activated astrocytes showing stretch sensitive channels with similar unitary conductance profiles but different gating properties. FIG. 3A is a representation of cell attached patch from adult astrocytes showing single channel recording above average patch currents. FIG. 3B is a representation of single channel recording for an outside out patch showing the presence of two to three channels. FIG. 3C is a representation of a unitary current-voltage plot fitted with a second-order polynomial showing inward rectification for channels in cell-attached patches (n=11). FIG. 3D is a representation of a unitary current voltage plot fitted with a second-order polynomial showing inward rectification for channels in outside-out patches (n=16).

FIGS. 5A–5D are representations of rate of blocking by GsMTx-4 as determined by superfusion of activated SACs in outside-out patches. FIG. 5A is a control trace (top) and current record in the presence of GsMTx-4 (bottom). The control trace was generated from 37 pressure steps applied to seven different patches held at −50 mV, with pressure levels ranging from 35–70 mm Hg. FIG. 5B is a superimposition of the average current records from 5A. FIG. 5C is the result of subtracting the control current race from the GsMTx-4 trace. FIG. 5D is the current trace during GsMTx-4 application fitted with a single exponential yielding a time constant of 594±10 ms. The fit is shown displaced from the data for clarity.

FIGS. 7A–G are representations of the effect of GsMTx-4 on whole cell swelling-activated current measured in astrocytes exposed to hypotonic saline. FIG. 7A shows resting whole-cell currents in isotonic saline produced by the waveform shown in 7E. (isotonic saline is normal bath saline with 80 mM NaCl replaced by 160 mM mannitol). Current scale bar is shown to the right. Swelling-activated currents were recorded after the cell had been exposed for 30 s to hypotonic saline. FIG. 7B is with isotonic saline minus 140 mM mannitol. FIG. 7C shows perfusion of hypotonic saline with 5 μM GsMTx-4. FIG. 7D shows swelling currents partially recovered about 4 minutes after washout of GMsTx-4. FIG. 7F shows peak swelling activated currents at 100 mV from two different cells (a and b) decreased over successive exposures to hypotonic solution. FIG. 7G shows an I–V plot of the average swelling-activated peak currents from six cells measured 30–40 s after hypotonic exposure.

FIG. 9A shows osmotic shrinkage in the control solution reduced both inward and outward currents. FIG. 9B shows that toxin reduced the inward currents in 1.0 T, but the currents in 1.5 T were unaffected. FIG. 9C shows shrinkage sensitive current due to inhibition of cationic SACs and anionic swelling currents. FIG. 9D show that the toxin did not affect membrane currents when SACs were inhibited by osmotic shrinkage.

FIG. 11 shows cDNA sequence for the gene encoding GsMTx-4. Translation of the gene is shown directly below the DNA sequence and each amino acid is aligned with its triplet codon. The first 21 amino acids are in bold and are the predicted signal sequence. The pro sequence is shown in box A followed by the GsMTx4 peptide outlined by the box B. The last two amino acids, which are removed during amidation, are in bold and italicized

DETAILED DESCRIPTION OF THE INVENTION

Figure 1A:
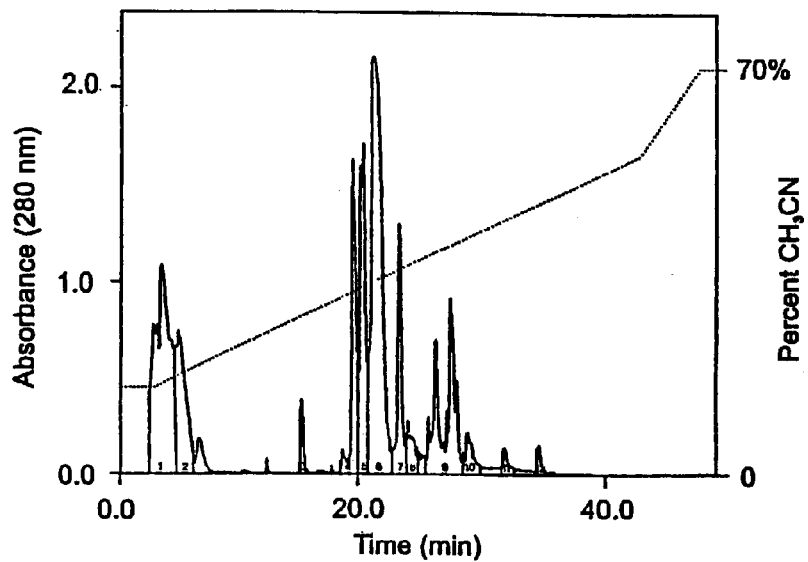
FIG. 1A is a chromatogram of *Grammostola* whole venom produced by a 40 minute linear gradient from 15–55% acetonitrile at a flow rate of 3.5 ml/minute. Pool fractions are labeled at the bottom. The percent acetonitrile is indicated by the dotted line overlaying the chromatogram.

The present invention discloses the identification, isolation and sequencing of a novel peptide present in the venom of *Grammostola spatulata*. The peptide has the following sequence.

GCLEFWWKCNPNDDKCCRPKLKC-SKLFKLCNFSFGK—(SEQ ID NO.2)

This peptide is designated herein as GsMTx-4. This peptide contains six cysteine residues and does not show significant homology to any other peptide toxin. The c-terminal amino acids, GK may form an amide resulting in the sequence disclosed below:

GCLEFWWKCNPNDDKCCRPKLKC-SKLFKLCNFSF—(SEQ ID NO:3)

Included within the scope of the present invention are variants of the peptide. The term "Variants" of the peptide for the purposes of specification and claims means peptides which have substitutions, additions or deletions in the sequence of SEQ ID NO:2 such that the resulting peptides exhibit SAC blocking activity and have a sequence which can form an inhibitor cystine knot (therefore has an ICK motif). In one embodiment, variants of the peptide are 34–36 amino acid in length.

Variants of the present invention include conservative substitutions of one hydrophobic residue for another, or the substitution of one polar residue for another such that the resultant peptide is capable of blocking SACs, Examples of conservative substitutions include the changes of: alanine to serine; arginine to lysine; asparagine to glutamine or histidine; aspartate to glutamate; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine. Those skilled in the art will also recognize that variants of the peptide can be made by addition or deletion of amino acids.

The peptides of the present invention have a structure determined from the sequence and NMR data, that show it to have 6–8 cystines that form an inhibitory cystine knot (the ICK motif). This motif is formed by 3 disulfides in a triple stranded β-sheet structure, which has one disulfide threaded through an embedded ring formed by the other two (for review see: Pallaghy, et. al., 1994. Protein Sci 3: 1833–1839; Norton, R. S. & P. K. Pallaghy, 1998. Toxicon 36: 1573–1583; Daly, N. L. & D. J. Craik. 2000. J Biol Chem 275: 19068–19075). This is a common toxin motif used by a variety of species including fungi, plants, marine molluscs, insects and spiders. While not intending to be bound by any particular theory, it is considered that the multiple disulfide bonds of the ICK motif fold small peptides into compact structures that are highly resistant to enzymatic digestion and form a useful rigid scaffolding for presentation of more flexible binding groups. The key binding residues generally reside at the outer surface. GsMTx-4 does not show >50% homology to any other published peptide toxin sequence. Other tarantula toxins which block voltage gated Ca$^{2+}$ and K$^+$ channels show the highest percentage of similarity to GsMTx-4

The peptides of the present invention can be formed by chemical synthesis or by molecular biology techniques such as site directed mutagenesis. An example of a variant which has SAC blocking activity is as follows

GCLEFWWKCNPNDDKCCRPKLKC-SKLFKLCNFSSG—(SEQ ID NO.1)

The present invention also discloses a method for purifying the peptide from spider venom and a method for using the peptide for blocking SACs. GsMTx-4 is useful for treatment of cardiac arrhythmias in mammals. It can be prepared by purification of the *Grammostola spatulata* venom. The venom is commercially available (Spider Pharm, Feasterville, Pa.) or may be elicited from the spider by standard techniques such as electrical stimulation.

GsMTx-4 can be isolated from spider venom by serial fractionation using standard chromatographic techniques. In a preferred embodiment, fractionation of the spider venom is carried out using reverse phase high performance liquid chromatography (HPLC). Reverse phase HPLC can be performed using C-8 or C-18 silica columns and trifluoroacetic acid/acetonitrile buffer system. C-8 and C-18 silica columns are commercially available (Mac-Mod Analytical, Inc., West Chester, Pa.).

The peptide GsMTx-4 and its variants can also be prepared by chemical synthesis using automated or manual solid phase methods. Such technologies are well known in the art. For example, such technologies are described in E. Atherton and R. C. Sheppard, Solid Phase Peptide Synthesis: A Practical Approach, IRL Press/Oxford Univeristy Press, Oxford, England, 1989; and M. Bodanzky, Peptide Chemistry: A Practical Textbook, Springer-Verlag, New York, N.Y., 1988. Thus, the peptide GsMTx-4 can be synthesized using Fmoc chemistry or an automated synthesizer. Depending upon quantitative yields, production of the linear reduced peptide can be performed in either a single process or in two different processes followed by a condensation reaction to join the fragments. A variety of protecting groups can be incorporated into the synthesis of linear peptide so as to facilitate isolation, purification and/or yield of the desired peptide. Protection of cysteine residues in the peptide can be accomplished using protective agents such as triphenylmethyl, acetamidomethyl and/or 4-methoxybenzyl group in any combination.

Further, the peptide GsMTx-4 may also be prepared by recombinant DNA technology. A DNA sequence coding for the peptide is prepared, inserted into an expression vector and expressed in an appropriate host cell. The expressed peptide can then be purified from the host cells and/or culture medium. Methods for preparing DNA coding for the peptide and expression of DNA are well known to those skilled in the art and are found for example, in Sambrook et al., (1989) Moelcular Cloning: A Laboratory Manual, Cold Spring Harbor, N.Y., S. L. Berger and A. R. Kimmel, Eds., Guide to Molecular Cloning Techniques: Methods in Enzymology, vol 152, Academic Press, San Diego, Calif., 1987, and in E. J. Murray, Ed., Gene Transfer and Expression Protocols: Methods in Molecular Biology, vol 7, Humana Press, Clifton, N.J., 1991. In addition, the cloning of a cDNA encoding the GsMTx-4 peptide is also disclosed.

The peptide GsMTx-4 of the present invention can be prepared for pharmaceutical use by incorporation with a pharmaceutically acceptable carrier or diluent. The peptide can be formulated into tablets, capsules, caplets and the like. Suitable carriers for tablets include calcium carbonate, starch, lactose, talc, magnesium stearate and gum acacia. The peptide can also be formulated for oral, parenteral or intravenous administration in aqueous solutions, aqueous alcohol, glycol or oil solutions or emulsions. The peptide can also be formulated for inhaling by encapsulating to facilitate alveolar absorption as has been done for insulin (Inhale Theraputic Systems, Zan Carlos, Calif., www. Inhale.com). Pharmaceutical compositions suitable for such routes of administration are well known in the art. For example, suitable forms and compositions of pharmaceutical preparations can be found in Remington's Pharmaceutical Science, 1980, 15$^{th}$ ed. Mack Publishing Co., Easton, Pa. Thus, the peptide GsMTx-4 can be administered orally, parentarally, intravenously, intramuscularly or intranasally. The peptide may also be applied to the tip of a catheter or other devices coming into contact with the heart during invasive procedures.

The amount of GsMTx-4 in the pharmaceutical composition can be determined by empirical methods. Those skilled in the art will recognize that the dosage administered to a particular individual will depend on a number of factors such as the route of administration, the duration of treatment, the size and physical condition of the individual, and the patient's response to the peptide including the side effects. Antiarrhythmic concentrations of another peptide toxin from spider venom are disclosed in U.S. Pat. No. 5,756,663.

As used herein the antiarrhythmic activity refers to the activity of the peptide GsMTx-4 in blocking stretch-activated channels in myocytes.

The following examples describe the various embodiments of this invention.

These examples are illustrative and are not intended to be restrictive.

EXAMPLE 1

This embodiment describes the isolation and molecular characterization of the peptide. For the isolation of the peptide, *Grammostola spatulata* (Theraphosidae) spiders were obtained from a captive population at Hogel Zoo (Salt Lake City, Utah). The arachnid species *Grammostola spatulata*, commonly referred to as the Chilean pink tarantula spider, is a member of the Theraphosidae family and the Chelicerata order. The *Grammastola* species have recently been reassigned to the genus *Phixotricus*, but *Grammastola* is used here to maintain consistency with prior biomedical publications. Venom was produced by an electrical milking procedure (Bascur et al., 1982, *Toxicon*, 20:795–796) and stored at −80 C. The venom was fractionated by high-performance liquid chromatography, incorporating Beckman System Gold 126 solvent delivery and 168 photodiode-array detector modules (Beckman Instruments, Fullerton, Calif.) using linear gradients with a flow rate of 3.5 ml/min unless noted. Whole venom (825 µl) was separated into eleven 75 µl aliquots that were each diluted to 2 ml each with 15% B. Solvent A was 0.1% TFA in water and solvent B was 0.1% TFA in acetonitrile. The diluted venom was fractionated on a (Zorbax RX—C8, 9.4×250 mm, 5 µm, 300 A; Mac-Mod Analytical, Inc., Chadds Ford, Pa.) reversed-phase (RP) column equilibrated in 15% B. The column was developed with a 40 min gradient (15–55% B) begun 3 min after injection of the sample with a flow of 3.5 ml/min. The effluent was monitored at 280 nm and fractions collected as noted on the chromatogram (FIG. 1A). Similar fractions from all eleven chromatographies were combined, lyophilized and tested for bioactivity. The assay samples were dissolved in 140 mM NaCl, 10 mM Hepes, 5 mM KCl, 2 mM MgSO4 to a final dilution of 1:1000, relative to whole venom, for testing on outside-out patches. Several of the pools showed partial block of the SACs (as described below), but only pool 9 gave consistent, complete block of the channels.

Figure 1B:
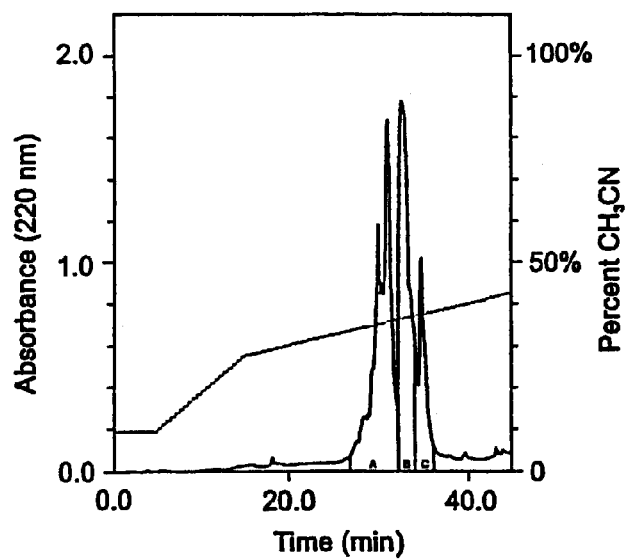
FIG. 1B is a chromatogram of fraction 9 from FIG. 1A.
Figure 1C:
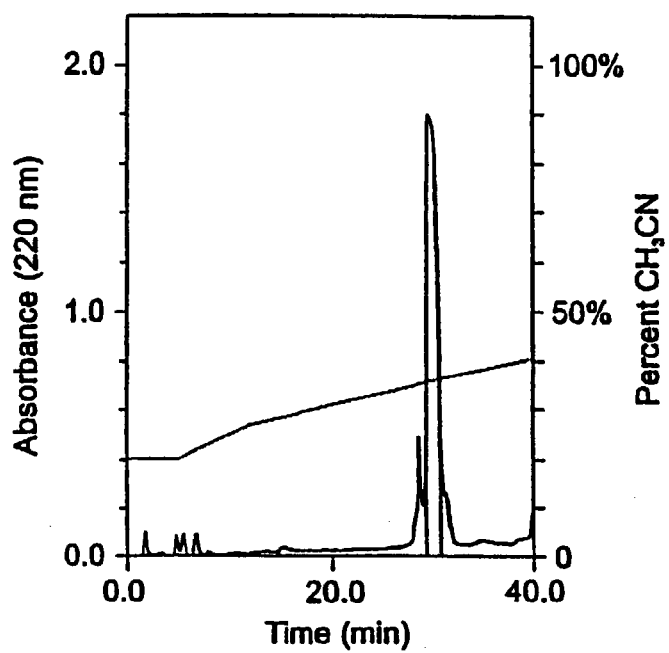
FIG. 1C is a chromatogram of fraction B from FIG. 1B.

Further purification of pool 9 (FIG. 1B) was achieved by RP chromatography on a Vydac C18 column (10×250 mm, 5 µm, 300 A; The Separations Group, Hesperia, Calif.) equilibrated in 10% B. Lyophilized pool 9 was dissolved in 4 ml of 10% B and chromatographed in 1 ml portions eluting with a 10 min gradient (10–28% B), followed by a 64 min gradient (28–60% B). The first gradient was begun 5 min after injection of the sample, the effluent was monitored at 220 nm and three fractions were collected. Corresponding fractions from the four chromatographies were combined, lyophilized and assayed as described above. Only pool B showed block of the SACs.

Figure 1D:
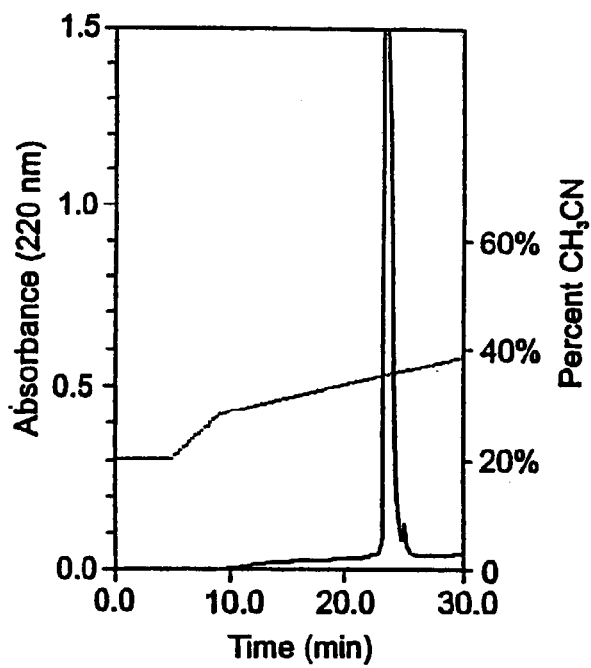
FIG. 1D is a chromatogram of the single peak from FIG. 1C.
Figure 3C:
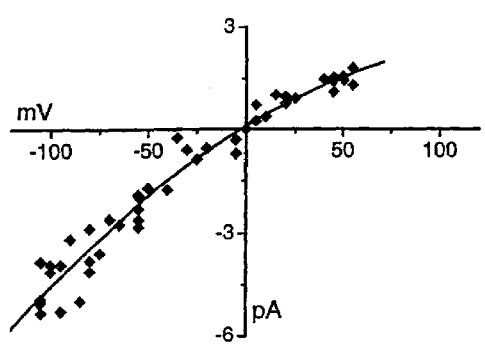

Therefore, pool B was subjected to a final RP chromatography to remove a small amount of earlier and later eluting peptides. Pool B was diluted to 4 ml with 20% solvent B and 0.5 ml portions chromatographed on the Zorbax column described above, eluting with a 7 min gradient (20–27% B), followed by a 46 min gradient (27–50% B) and the effluent was monitored at 220 nm (FIG. 3C). The first gradient was begun 5 min after injection of the sample. The active peptide, GsMTx-4 eluted between 29.5 and 30.5 min. Corresponding fractions from the eight chromatographies were pooled to give 7.5 mg of GsMTx-4. The average yield of GsMtx-4 from several purifications was 8 mg/ml of venom fractionated, which corresponds to a concentration of 2 mM in whole venom. The purity of the final product used in single channel and whole cell assays was assessed by analytical chromatography (Aquapore RP300 C8 column, 4.6×150 mm, 5 um, 300 Å; PE Biosystems, Forest City, Calif.) eluting with a 40 min linear gradient (15–55% B) with a flow of 1 ml/min monitored at 220 nm (FIG. 1D). Elution with a gradient of methanol/water (0.1% in TFA) gave a similar profile with a longer retention time, but revealed no other impurities.

The peptide was further purified by microbore reverse phase-HPLC (0.8 mm×250 mm C18 column, with a linear gradient from 0.1% TFA-15% $CH_3CN$ to 0.1% TFA-70% $CH_3CN$ in 90 min, flow rate 40/µl/min, monitored at 214 nm). The toxin peak was collected at 24.6 min. The HPLC fraction (~1 nmol) was dried down and taken up in 80 µl 8 M guanidine HCL-100 mM TRIS-5 mM tributylphosphine at pH 8.5 and incubated for 8 h at 55° C. N-isopropyliodo-actamide (1 mg in 20 µl MeOH+80 µl TRIS) was added and the solution was incubated for an additional 2 h at room temperature. The reduced and alkylated peptide was then desalted by HPLC on a C18 column as described above (elution time 30.1 min). N-terminal sequencing was carried out on an ABI 477 after loading the reduced and alkylated peptide on PVDF membrane.

Digestion with BNPS-skatole (Fontana, 1972) was carried out by dissolving the purified reduced and alkylated peptide in 50 ul 0.1% TFA and 15 µl BNPS-skatole. The solution was incubated at room temperature for 8 h. The digestion products were separated by HPLC as described above. Two main peaks were collected and sequenced by Edman degradation. Asp-N digestion (Wilson 1989) was performed by dissolving the purified reduced and alkylated peptide in 100 mM TRIS, pH 8.0 and treating with 1% (w/w) Asp-N for 20 h at 35 C. The fragments were separated and analyzed by mass spectrometry prior to Edman degradation.

For determination of the molecular weight by mass spectrometry, one micro-liter of the sample solution (intact toxin or fragments) in 0.1% TFA (or the HPLC elution solvent) was mixed on the sample plate with 1.0 µl of a saturated solution of 4 hydroxy-α-cyanocinnamic acid in 1:1 $CH_3CN$: 0.1% aq.TFA. The solution was air dried before introduction into the mass spectrometer. Spectra were acquired on a PerSeptive Biosystems Voyager Elite MALDI-TOF (matrix assisted laser desorption ionization-time of flight) instrument operated in linear reflectron delayed extraction mode (50–100 nsec). The instrument was equipped with a nitrogen laser (3 nsec pulse). The acceleration potential was 22 kV.

MALDI-MS analysis showed the molecular weight of the native toxin was 4093.90 (MH+ ion). The alkylated and reduced toxin displayed a peak at m/z 4690, indicating 3 disulfide bonds or six cysteine residues were present. N-terminal sequencing was followed by sequencing of two different C-terminal fragments produced by enzymatic digests with BNPS-skatole and Asp-N. The predicted mass up to, but not including the C-terminal amino acid, is 4019.85 if the protons for 3 disulfide bonds are subtracted. The difference between the measured unprotonated mass of 4092.9 and the latter (4019.85) is 73.05, which is the mass of a glycine-amide. The mass accuracy of the MALDI-MS analysis is approximately +0.1 D with internal calibration. The final sequence shown in FIG. 2 (also SEQ ID NO:1) is 35 amino acids in length with the C-term glycine amide added.

The six cysteine residues form an ICK motif commonly observed in many other peptide toxins from both terrestrial and aquatic animal venoms (Narasimhan et al., 1994, *Nature Structural Biol.*, 1:850–852; Norton et al., 1998, *Toxicon*, 36:1573–1583). GsMTx-4 shows less than 50% homology to any other peptide toxin. Other tarantula toxins which block voltage gated $Ca^{2+}$ and $K^+$ channels show the highest percentage of similarity to GsMTx-4 as illustrated by the amino acid alignment in FIG. 2. A $K^+$ channel toxin labeled protein 5 from *Brachypelma smithii* (Kaiser et al., 1994, *Toxicon*, 32:1083–1093; Norton et al., 1998, supra) shows ~50% total sequence similarity. The most significant regions of homology occur within the cysteine motif. Besides the conserved cysteine motif, there are 3 other residues (F4, D13 and L20) that are conserved in all five toxins. Like the positively charged-conotoxin and -agatoxin families of $Ca^{2+}$ channel blockers, GsMTx-4 carries an overall positive charge (+5).

EXAMPLE 2

This embodiment describes the effect of the peptide GsMTx-4 variant (SEQ ID NO:1) on SACs. To illustrate this, adult rat astrocytes which are known to have SACs, were used. Adult rat astrocytes were cultured according to standard methods. Briefly, activated adult astrocytes isolated from gelatin-sponge implants from adult Sprague-Dawley rat brains obtained according to the method of Langan et al. (1995, *Glia*, 14:174–184) were used at passage numbers 2–4. Astrocytes were maintained in DMEM, 10% fetal bovine serum and 1% Penicillin/Streptomycin and were used in experiments between 2 and 5 days after passage. Cells between passage 4 and 35 expressed SACs with the same properties Both stellate process bearing cells and flat polygonal (fibroblast-like) cells were used.

The cultured astrocytes were used for single channel and whole cell recorndings. For single channel patch clamp, patch voltage was controlled by an Axopatch 200B (Axon Instruments, Calif.) and currents were recorded directly onto computer disk via a Labmaster DMA Ver. B (Scientific Instruments, Calif.) board controlled by pClamp6-Clampex acquisition software (Axon Instruments, California). Currents were sampled at 10 KHz and low-pass filtered at 2 KHz through the 4 pole Bessel filter on the Axopatch 200B. Experimental voltage protocols were controlled by pClamp6-Clampex. All potentials are defined with respect to the extracellular surface.

Electrodes were pulled on a Model PC-84 pipette puller (Brown-Flaming Instruments, Calif.), painted with Sylgard 184 (Dow Corning Corp. Midland Mich.) and fire polished. Electrodes were filled with KCl saline (KCl 140 mM, EGTA 5 mM, $MgSO_4$ 2 mM, Hepes 10 mM, pH 7.3) and had resistances ranging from 3–8 MWBath saline consisted of NaCl 140 mM, KCl 5 mM, $MgSO_4$ 1 mM, $CaCl_2$ 1 mM, glucose 6 mM and Hepes 10 mM, pH 7.3.

Pressure and suction were applied to the pipette by a pressure clamp. Pressure values represent pressure in the pipette, i.e., the intracellular side of the membrane in out-side-out patches. Suction applied to a cell-attached patch has the same sign as pressure applied to an outside-out patch. The rise time of pressure changes at the tip were determined by monitoring the rate of current change when pressure steps were applied to an electrode containing 150 mM KCl solution and placed in a water bath. The $t_{10-90}$ was ~5 ms as determined by exponential fits to the current decay. Perfusion of toxin samples was performed by a pressurized bath perfusion system BPS-8 (ALA scientific instruments, NY) with 8 separate channels.

Off-line data analysis was performed with pClamp6 analysis software and Origin 5.0. Maximal unitary channel currents were determined via Guassian fits to the peaks of all points amplitude histograms generated from records containing 1–3 channels. Many current records displayed more than 3 channel openings (maximal single channel currents plus subconductance states) and were impossible to fit using Pstat software. Some of these records were analyzed by determining all of the step-like changes in current during the pressure application and selecting the average maximal current level as the unitary current. The data analyzed by this method was in good agreement with the unitary current levels determined by analysis of all points amplitude histograms from single channel patches.

The presence of stretch-activated channels in the astrocytes is shown in FIGS. 3(A–D). Representative single channel current recordings are shown above average patch currents from a cell-attached patch (A) containing a single channel, and an outside out patch (B) containing 2–3 channels. Cell-attached patch recordings were made with 140 mM KCl pipette saline, and outside-out patch recordings are with symmetrical 140 mM KCl pipette solutions. Pressure steps (indicated by the bar at the top) were applied to the patches at different holding potentials shown to the left of each recording. Voltages are relative to the extracellular side. Average current records were calculated from multiple pressure steps (ranging from 5–15 steps) at each voltage. In cell-attached mode, channel adaptation, lower $P_O$ and multiple sub-conductance states are apparent at negative potentials. Channels in outside-out patches from astrocytes show slow voltage dependent activation and lower $P_O$ at negative potentials. Unitary current-voltage plots were fitted with a second order polynomial and show inward rectification for channels in cell-attached (C, n=11 patches) and outside-out (D, n=16 patches) patches. Voltages for cell-attached data points were corrected for the average resting membrane potential measured in the whole cell configuration. Each point represents an average current calculated from applying multiple pressure steps to a single patch.

These data indicate that in cell-attached patches, activated adult astrocytes express primarily one type of SAC that can be activated by both pressure and 15: suction (FIG. 3A, only pressure data shown). Observation from more than 100 patches typically showed 2–5 channels/patch. SAC activity in cell-attached patches was sensitive to the level of suction used in seal formation. Channels were rarely observed when >10 mmHg of suction was used during seal formation, whereas >90% of patches showed channel activity with <10 mmHg. With 140 mM KCl in the electrode, the single channel conductance inwardly rectified being 46 pS at −100 mV, but only 21 pS at +100 mV (FIG. 3C). Channel activity was normally initiated by applying between 25–35 mmHg of suction. However, rundown did occur so that increasing levels of suction were required to activate the channels over the 5 to 10 minutes during which data was acquired.

The open probability ($P_O$) was time and voltage dependent, displaying a fast adaptation (within 100 ms at hyperpolarized potentials) similar to that reported for Xenopus oocytes (Hamill et al., 1992, Proc. atl. Acad. Sci. USA, 89:7462–7466). The time dependence of $P_O$ can be described by an initial phasic period followed by a tonic period as defined in (Bowman et al., 1996, Brain Res., 584:272–286). Both the duration of the phasic period and $P_O$ during the tonic period showed a steep voltage dependence, decreasing as the potential becomes more negative (FIG. 3A, see average currents). Out of 16 cell-attached patches analyzed, 12 displayed adaptation at hyperpolarized potentials. In addition to adaptation, multiple voltage-dependent substates are visible at −100 mV, compared to only one at depolarizing potentials.

Figure 3D:
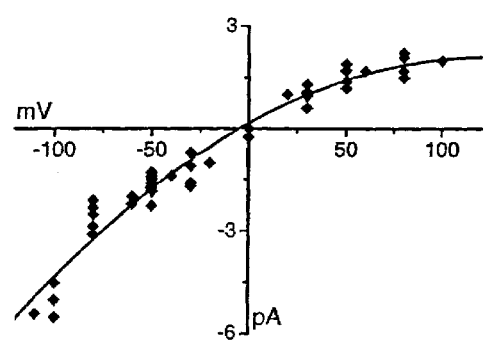

Although SACs had different adaptation properties in outside-out patches, channel activity was generally similar to that in cell attached patches. The SACs opened in response to both pressure and suction (FIG. 3B). With 140 mM KCl in both the pipette and bath the I–V profile (44 pS at −100 mV, and 21 pS at +100 mV, cytoplasmic side) was nearly identical to that observed for cell-attached patches (FIG. 3D). In this configuration the channels were initially activated by between 30–40 mmHg of pressure. The similarities between the conductance and pressure sensitivity in the two patch configurations suggest that these channel properties have not been significantly modified by outside-out patch formation. However, out of 12 outside-out patches, only 1 displayed the fast adaptation property observed in cell-attached patches. Instead, 2 showed no change in $P_O$ with respect to time or voltage, while the remaining 9 patches exhibited a slow increase in current at both positive and negative voltages where the number of active channels increased during the 500 ms pressure step (see FIG. 3B 100 mV, and FIG. 5A average control current). The rate of increase was greater for pressure steps at positive voltages due to an increase in $P_O$ at positive potentials. The single channel conductance and inward rectification observed here were similar to the properties reported for the family of nonselective cation SACs (for review see:Yang et al., 1993, In:Non-selective ion channels. D. Siemen and J. Hescheler, Eds. Springer Verlag, Heidelberg. pp 79–92). These data indicate that outside-out patches can be used for the study of modulation of SAC function.

Figure 4:
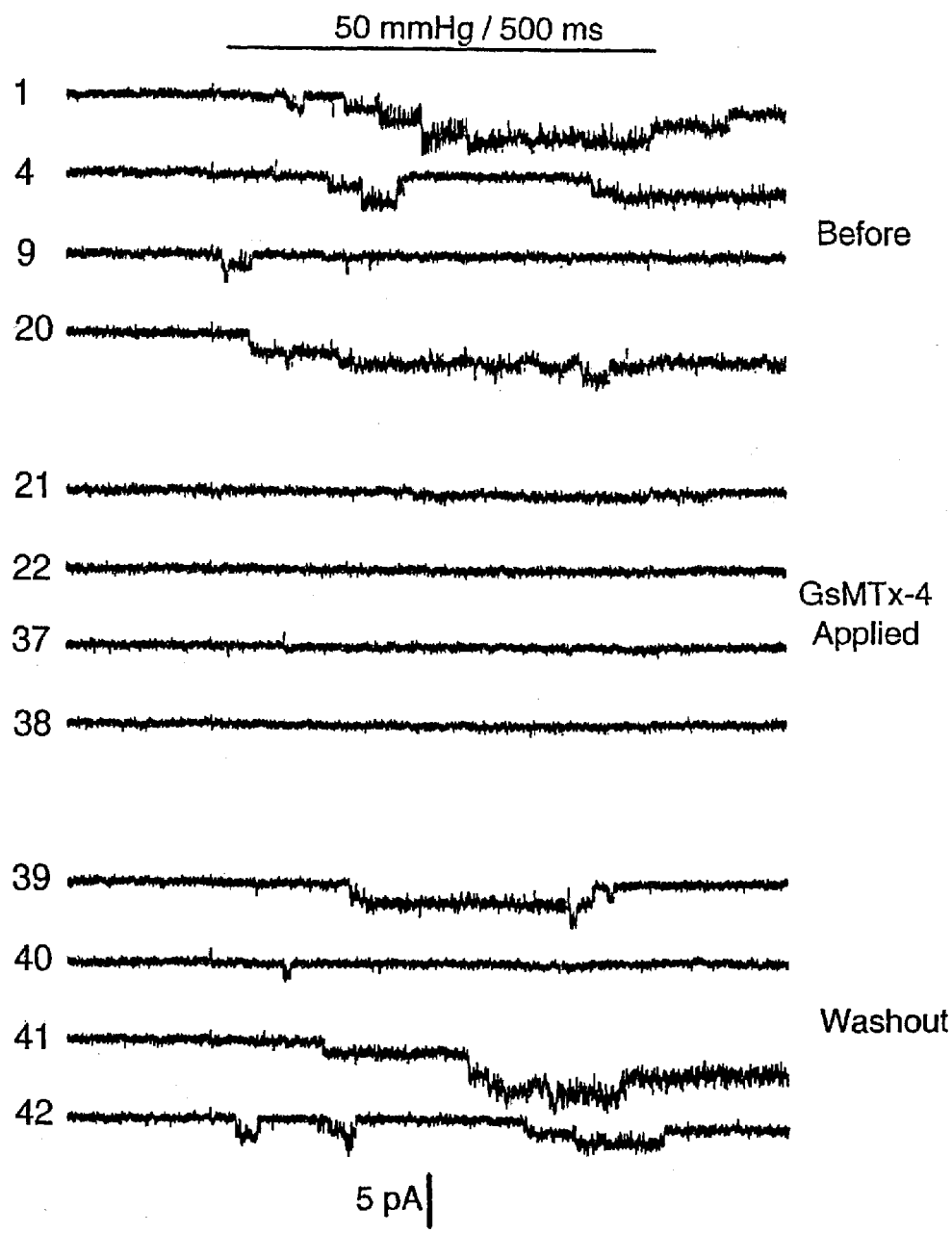
FIG. 4 is a representation of blockage of SACs by GsMTx-4 in outside-out patches.

The outside out patches from adult astrocytes as described above were used for testing the HPLC fractions obtained in Example 1. The HPLC fractions were lyophilized, redissolved at a 1:1000 dilution and perfused onto outside out patches. Fraction 9 from FIG. 1A completely blocked SACs. The fraction containing the single peak in FIG. 1D was then tested for activity against SACs. The results are shown in FIG. 4. With this fraction, the block was complete, and occurred rapidly upon superfusion of the patch as shown by representative current traces in FIG. 4. The patch was held at −50 mV, and the pressure pulse is shown above the records.

The entire experiment is comprised of 60 pressure steps: steps 1–20 occur before GsMTx-4 application; steps 21–38 while GsMTx-4 is being perfused; steps 39–60 occur during washout. Each 500 ms pressure step was separated by 1.5 seconds at 0 pressure. Four representative records from each stage of the experiment are displayed. Other peptides have been isolated from the spider venom which are active against SACs (such as, GsMTx-1, described in U.S. Pat. No. 5,756,663), however GsMTx-4 showed the most consistent and potent activity.

The association rate of the toxin was determined by applying GsMTx-4 to an outside-out patch while the channels were activated by stretch (FIG. 5). Average SAC currents were calculated from 3-second pressure steps indicated by the bars above the traces (A). The control trace was generated from 37 pressure steps applied to 7 different patches held at −50 mV, with pressure levels ranging from 35–70 mmHg. The current increased exponentially over the 3-second pressure application. The GsMTx-4 response was produced by applying 5 μM toxin one second after the onset to the pressure step indicated by GsMTx-4 bar. The GsMTx-4 current record was averaged from 29 pressure steps to 6 different patches held at −50 mV, with the steps ranging between 38–80 mmHg. Currents were nearly identical over the first second of the average current records as shown when the two are superimposed in (B). Subtracting the control current trace from the GsMTx-4 trace produced the difference current in (C). The current trace during GsMTx-4 application was fitted with a single exponential yielding a time constant of 594±10 ms (D). The fit is shown displaced from the data for clarity.

In the absence of GsMTx-4, channel activity increased over time at constant pressure (compare FIG. 3B with FIG. 5A). When 5 µM toxin was perfused onto the patch one second after the initiation of the pressure step, the current decayed exponentially (FIG. 5A, GsMTx-4). When the control and GsMTx-4 average current records are superimposed, the first second before GsMTx-4 application shows that the rate and amount of current increase are nearly identical (FIG. 5B). The difference current was calculated (FIG. 5C) and the period during which 5 µM GsMTx-4 was applied was fitted with a single exponential (FIG. 5D) yielding a time constant of 594±10 ms. Assuming a 1:1 binding, this gives an association constant, $k_A$, of $3.4 \times 10^5$ $M^{-1}s^{-1}$.

Figure 6A:
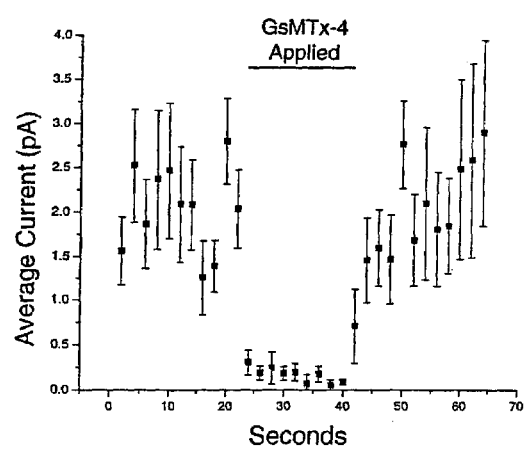
FIG. 6A is a representation of the dissociation rate of GsMTx-4, determined from the recovery rate of SAC current on washout. SAC currents were activated by 500-ms pressure steps at 2-s intervals in outside-out patches held at −50 mV.
Figure 6B:
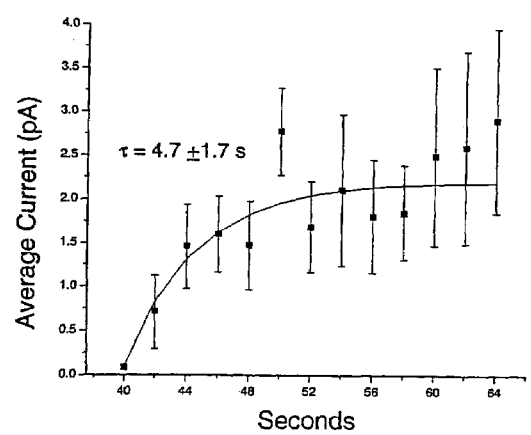
FIG. 6B shows the recovery kinetics fitted to a single exponential with a time constant of 4.7±1.7 s.

To determine the dissociation rate, the average patch current due to the opening of SACs was monitored before, during and after GsMTx-4 application from 7 different patches (FIGS. 6A and 6B). SAC currents were activated by 500 ms pressure steps at 2 second intervals in outside-out patches held at −50 mV. FIG. 6A represents the average current (±standard error) from 7 different patches. The recovery kinetics were fitted to a single exponential with a time constant of 4.7±1.7 seconds (FIG. 6B). From this dissociation constant ($k_d$=0.21 $s^{-1}$) and the association constant determined above ($k_a$=3.3×10$^5$ $M^{-1}$ $s^{-1}$), the calculated equilibrium constant, $K_D=k_d/k_a$=631±240 nM (standard error calculated from the first order approximation using the errors of $k_a$ and $k_d$). Using the ratio of rate constants to evaluate $K_D$ minimizes errors caused by rundown. The mean SAC current was 2.04±0.14 pA (SE) over 11 pressure steps prior to GsMTx-4 application (FIG. 6A). When GsMTx-4 was applied, the average current dropped to 0.17±0.02 pA. The average current over the last 8 pressure steps (10 seconds after GsMTx-4 washout) returned to the initial current level of 2.28±0.17 pA. For a single binding site, Michealis-Menton knetics predicts the ratio of the blocked to the unblocked current is $I/I_0=1(1+K_d/S)$, where S is the substrate (peptide) concentration and $K_d$ is the equilibrium dissociation constant. Using the data from FIG. 6, $I/I_0$=0.083, which gives a binding constant $K_d$=415 nM, consistent with the value calculated from the ratio of association and dissociation rates. There is no significant difference between whole-cell currents in isotonic saline and currents measured between 30 and 120s after perfusion with 5 µM GsMTx-4. In contrast to GsMTx-4, CsCl produces a significant decrease in current at hyperpolarized potentials.

EXAMPLE 3

This example demonstrates the effect of GsMTx-4 on whole-cell swelling activated currents. It is considered that part of the swelling activated currents are attributable to SACs. To illustrate this embodiment, adult rat astrocytes were cultured as described above. Whole cell current was measured by the Nystatin perforated patch. Bath saline was the same as in Example 2. Pipette saline consisted of: KCl 80 mM, $K_2SO_4$ 30 mM, NaCl 10 mM, $MgSO_4$ 3 mM, $CaCl_2$ 0.13 mM, EGTA 0.23 mM and Hepes 10 mM, pH 7.3. Nystatin was dissolved in pipette saline to a final concentration of 200 mg/ml. After patch formation, access resistance was allowed to drop to ~15 MW (uncompensated), after which the series resistance compensation was set at ~65%, and prediction was set to ~75%. Whole cell capacitance measurements ranged from ~25–50 pF. Whole cell currents were monitored by either a voltage step protocol shown in FIG. 7, or by 600 ms voltage ramps. During hypotonic swelling the cell was perfused initially with isotonic saline (bath saline with 160 mM mannitol replacing 80 mM NaCl) before switching to hypotonic saline (isotonic saline minus 140 mM mannitol). The BPS-8 perfusion system was used to rapidly (<200 ms) change the bathing solution. Peak currents were measured at 3–5 ms into voltage steps.

Figure 7F:
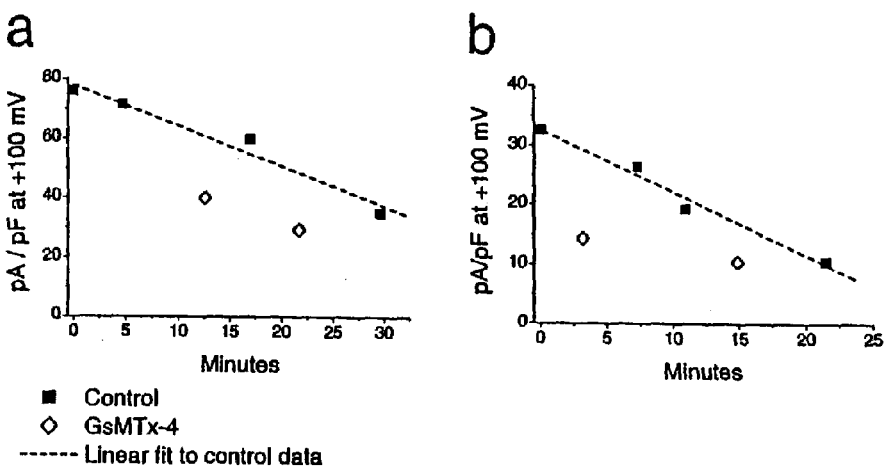
Figure 7G:
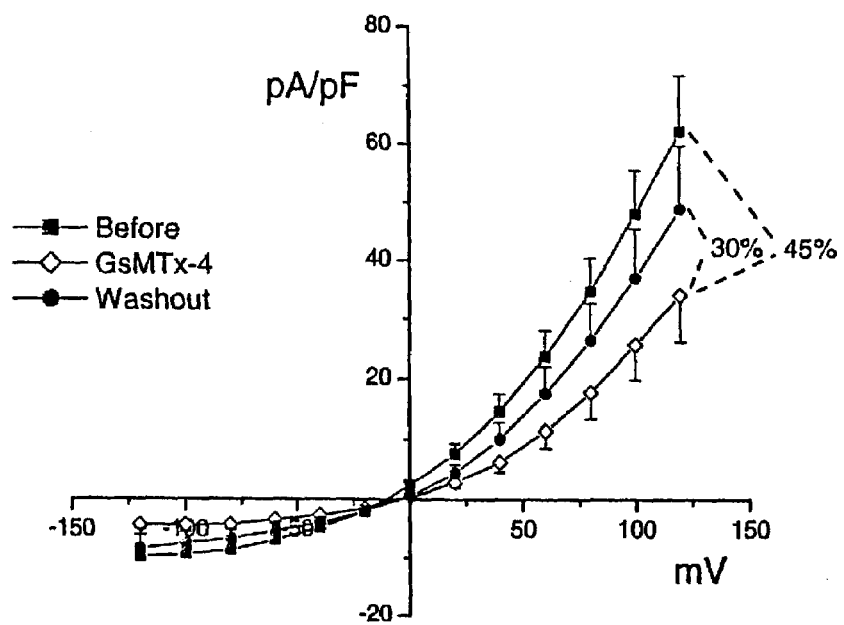
Figure 8:
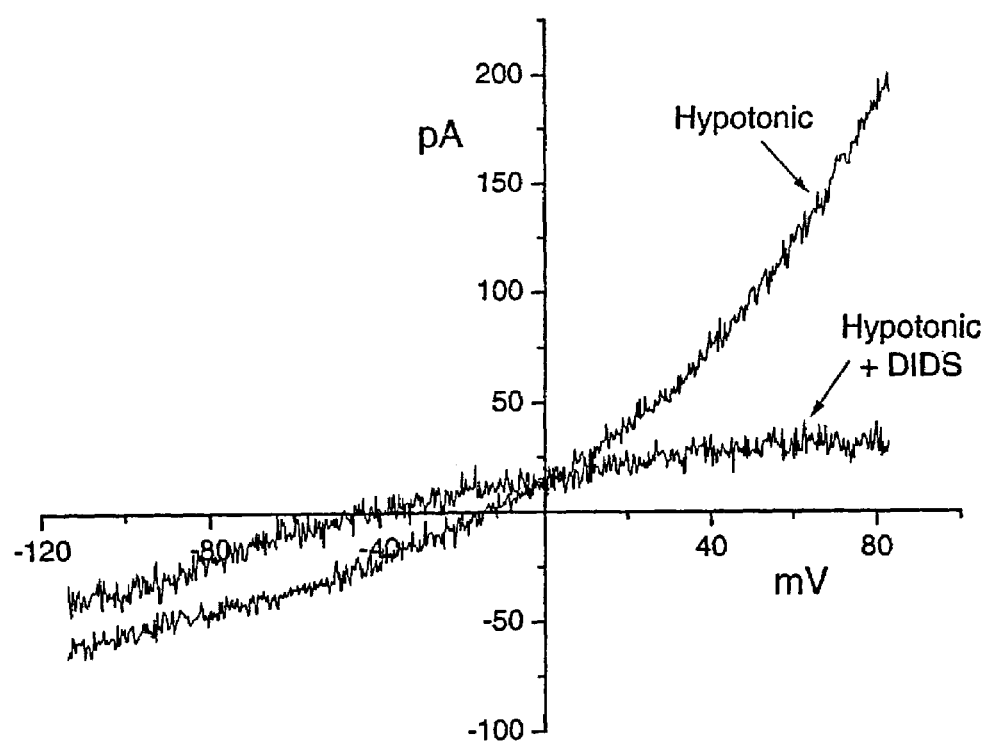
FIG. 8 is a representation of the effect of DIDS on swelling-activated currents in adult astrocytes.

As shown in FIGS. 7A–G, the peptide GsMTx-4 reduces whole cell swelling activated currents. After 30 seconds exposure to hypotonic conditions, adult astrocytes display a similar large conductance increase that slowly inactivates at large depolarizing voltages as shown by perforated patch whole cell current recordings (compare FIG. 7A resting current to FIG. 9B swelling-activated current). During hypotonic exposure, cells were held at −50 mV prior to I–V test voltage steps to reduce the influence of voltage gated $Ca^{2+}$ channels on $Ca^{2+}$ influx. The swelling activated current has a large anionic component since 50 µM DIDS produced a significant reduction in current (especially at depolarized potentials) and an average −33 mV (n=6) shift in the reversal potential (FIG. 8). A residual current with a reversal potential shifted toward $E_K$ remained. Applying 5 µM GsMTx-4 while hypotonically swelling the cell significantly reduced the peak current response by about 75% at 30 seconds after hypotonic exposure (FIG. 7C). After washout of GsMTx-4, the swelling currents partially recovered. A hypotonic stimulus produced larger swelling-activated currents, although not of the same magnitude as the original control stimulus (FIG. 7D). This reduced response after washout is not due to lingering toxin effects, since >3 min of washout separated successive hypotonic stimuli. Instead, it was observed that the response to successive hypotonic exposures slowly decreased over time (FIGS. 7Fa and b). Representative peak current responses from two different cells displayed a roughly linear decrease in swelling-activated current (FIG. 7F). GsMTx-4 always reduced the swelling-activated current from the control response (FIG. 7F, ◇). However, in light of the slowly degrading hypotonic response, it was necessary to estimate the amount of GsMTx-4 block by subtracting it from the mean "before" and "after" control hypotonic stimuli. The I–V profiles for the swelling-activated difference currents in FIG. 7G show a clear difference between the before (+nd after (●) control responses. The percent block produced by GsMTx-4 (◇) relative to each of the control curves is shown to the right. The estimated reduction in swelling-activated current produced by 5 µM GsMTx-4 was similar at both hyperpolarizing and depolarizing potentials (~48% at −100 mV and ~38% at +100 mV). Furthermore, unlike DIDS which produced a large (−33 mV) shift in reversal potential due to the specific loss of anionic current, GsMTx-4 produces almost no change in reversal potential (+2 mV, statistically indistinguishable from 0 mV). These data demonstrate that the peptide GsMTx-4 blocks SACs in swelling activated currents.

EXAMPLE 4

This example demonstrates that the peptide GsMTx-4 affects stretch/swell induced currents in a model for congestive heart failure. Ventricular myocytes were freshly isolated from New Zealand white rabbits with aortic regurgitation induced congestive heart failure using a collagenase-pronase dispersion method (Clemo et al., 1997, supra). Cells were stored in a modified Kraft-Bruhe solution (KOH 132 mM, glutamic acid 120 mM, KCl 2.5 mM, $KH_2PO_4$ 10 mM, $MgSO_4$ 1.8 mM, $K_2$EGTA 0.5 mM, glucose 11 mM, taurine 10 mM, Hepes 10 mM, pH 7.2). Myocytes were used within 6 h of harvesting and only quiescent cells with no evidence of membrane blebbing were selected for study.

Swelling activated currents were measured in myocytes according to the method of Clemo & Baumgarten (1997). Briefly, electrodes were pulled from glass capillaries to give a final tip diameter of 3–4 mm and a resistance of 0.5–1 MW when filled with the standard electrode filling solution (K aspartate 120 mM, KCl 10 mM, NaCl 10 mM, MgSO$_4$ 3 mM, Hepes 10 mM, pH 7.1). Whole cell currents were recorded using an Axoclamp 200A. Pulse and ramp protocols, voltage clamp data acquisition and off-line data analysis were controlled with software written in ASYST. Both step and ramp voltage clamp protocols were applied with a holding potential of –80 mV. Currents were digitized at 1 KHz and low-pass filtered at 200 Hz. Whole cell currents were recorded using the amphotericin perforated patch technique. Solution changes were performed by bath perfusion that was completed within 10 s. The standard bath solution contained (NaCl 65 mM, KCl 5 mM, CaSO$_4$ 2.5 mM, MgSO$_4$ 0.5 mM, glucose 10 mM and Hepes 10 mM pH 7.2, and 130 mM (IT) or 283 mM (1.5 T) mannitol to control the osmolarity. Isotonic osmolarity was taken as 296 mosm (IT) and 444 mosm for hypertonic solution (1.5 T).

Figure 9A:
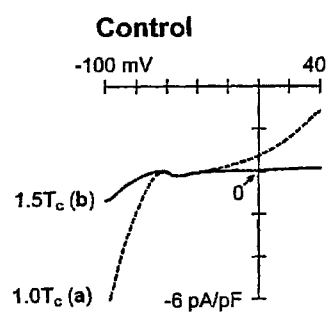
FIGS. 9A–D are representations of ionic currents (A–C) and cell volumes (D) measured during perforated patch voltage clamp ($E_{hold}$=−80 mV) of ventricular myocytes from rabbits with aortic regurgitation-induced CHF.
Figure 9B:
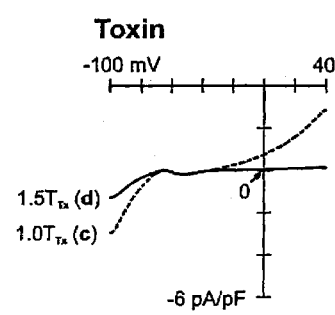
Figure 9C:
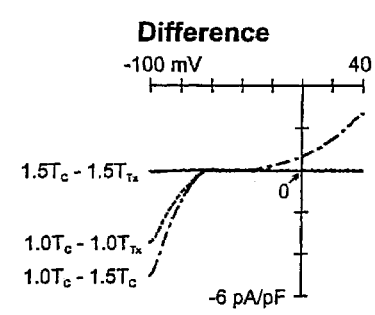

The myocytes were exposed to 1.0 T and 1.5 T solution in the absence (1.0 T$_C$, 1.5 T$_C$) and presence (1.0 T$_{TX}$, 1.5 T$_{TX}$) of 0.4 µM GsMTx-4. As shown in FIG. 9, at 0.4, GsMTx-4 produced a significant reduction of the inward I$_{Cir,swell}$, but had no effect on the outward I$_{CI,swell}$ (FIG. 9Bc). However, whole cell current was unaffected by GsMTx-4 when swelling-activated currents were inactivated by 1.5 T hypertonic saline (FIG. 9Bd). The difference currents in FIG. 9C show that GsMTx-4 blocked only inward swelling-activated current (compare: FIG. 9C, 1.0$_{TC}$–1.5 T$_C$ (total I$_{Cir,swell}$) to 1.0 T$_C$-1.0 T$_{TX}$ (toxin sensitive I$_{Cir,swell}$)). The remaining inward current is largely. I$_{CI,swell}$. The toxin produced no further reduction in the presence of hypertonic saline when swelling activated current is turned off (FIG. 9C, 1.5 T$_C$-1.5 T$_{TX}$).

Figure 9D:
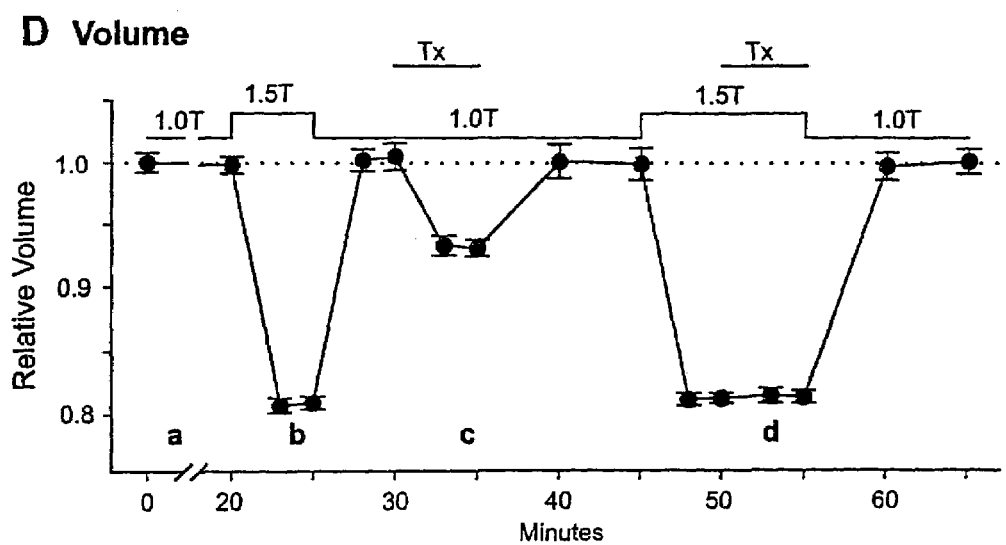

Myocyte volume was determined by visualization with an inverted Nikon Diaphot microscope equipped with Hoffman modulation optics and a high resolution TV camera coupled to a video frame-grabber. Images were captured on-line each time a ramp or step voltage clamp protocol was performed using a program written in C and assembler and linked to ASYST voltage-clamp software. A combination of commercial (MOCHA; SPSS) and custom (ASYST) programs were used to determine cell width, length, and area of the image. The results of volume changes are shown in FIG. 9D. GsMTx-4 produced a cell volume reduction that is ~40% of that produced by 1.5 T hypotonic saline. These data indicate that GsMTx-4 blocks stretch activated channels in swelling activated currents.

EXAMPLE 5

Figure 10A:
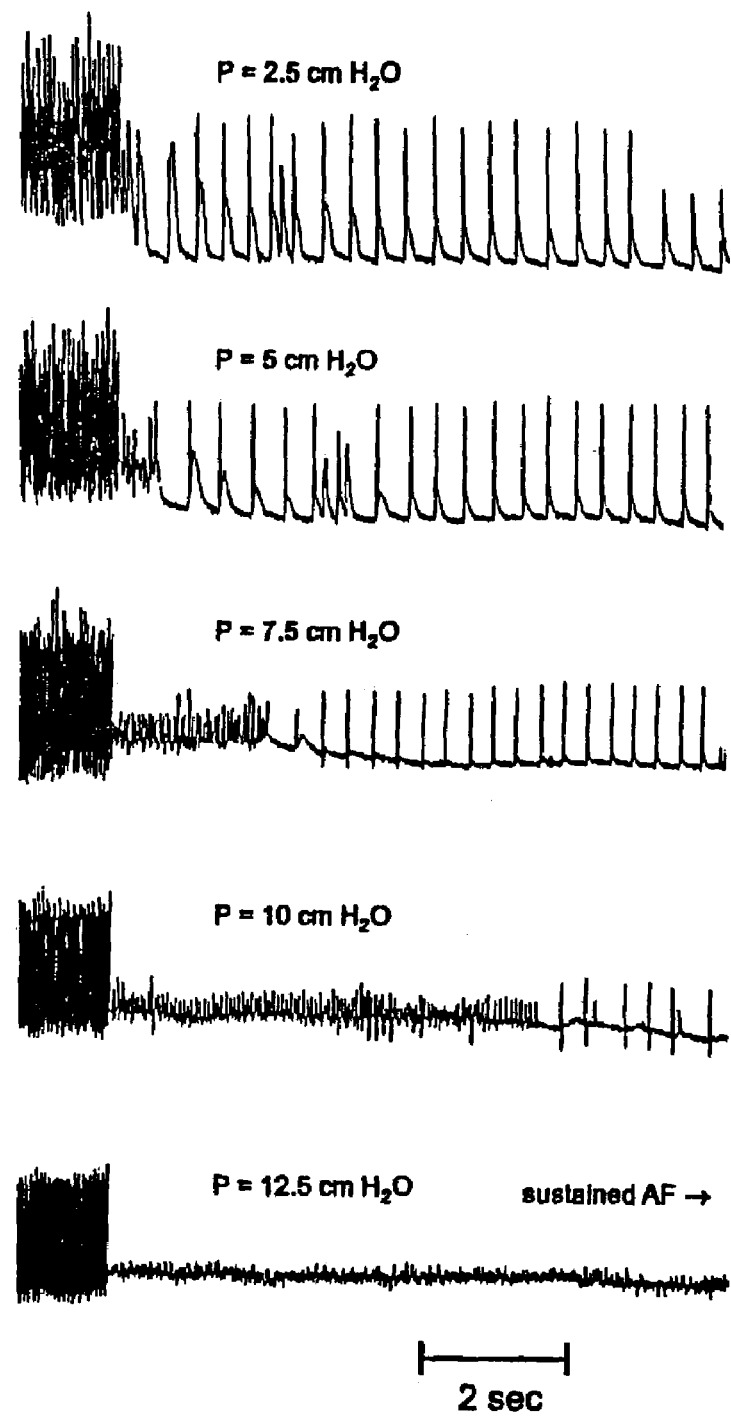
FIG. 10A is a representation of bipolar electrograms showing an incerase in atrial fibrillation (AF) with pressure, becoming sustained at 12.5 cm $H_{20}$.
Figure 10B:
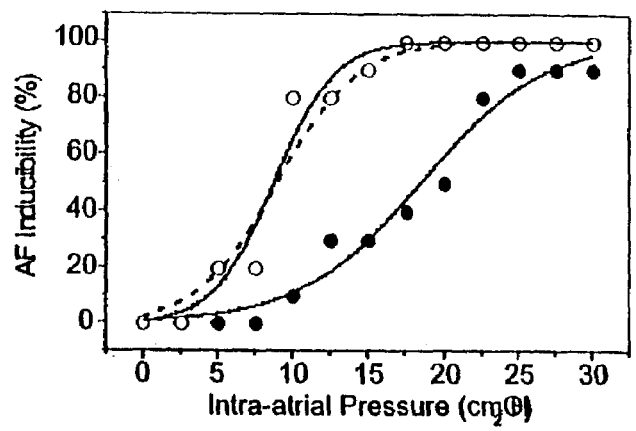
FIG. 10B is a representation of the induction of AF lasting more than 2 seconds for control (O) and in the presence of 170 nM GsMTx-4 (●). Dashed line indicates the response after 20-min washout.
Figure 10C:
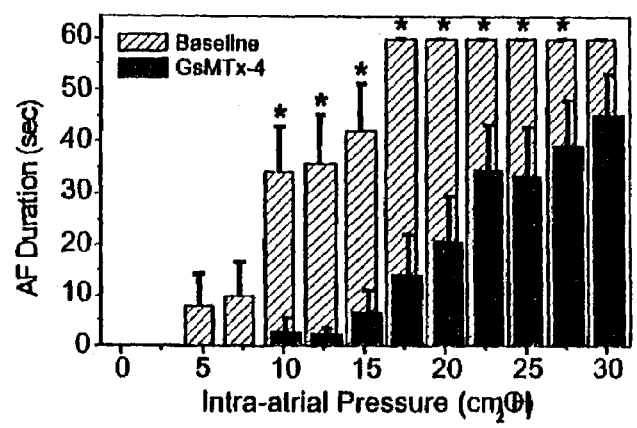
FIG. 10C shows the duration of AF (n=7) as a function of pressure (mean±standard error). GsMtx-4 (170 nM) decreased the average time to spontaneous recovery from AF (asterisks, P less than 0.05).
Figure 10D:
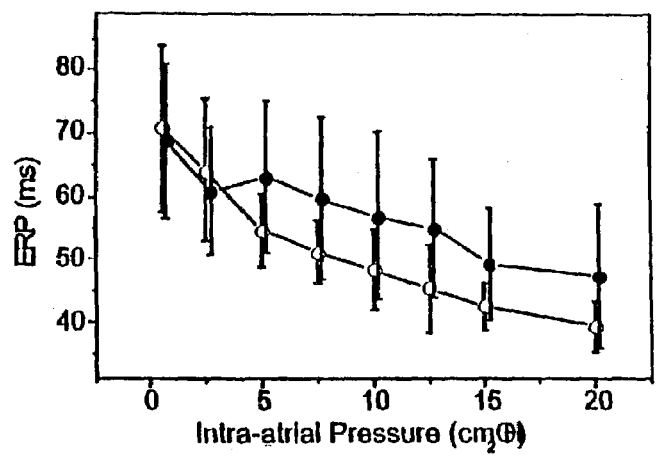
FIG. 10D shows that GsMtx-4 did not block stretch-induced shortening of the refractory period (n=10).

This example demonstrates that the peptide of the present invention can be used against cardiac fibrillation. To illustrate this embodiment, fibrillation was initiated in perfused rabbit hearts with a burst of high-frequency stimulation FIG. 10A. Stretching the atrium chamber increased the incidence and duration of fibrillation (FIG. 10A–C). At pressures above 12 cm H$_2$O, the fibrillation became sustained and the probability of sustained fibrillation (for, longer than 60 s) approached unity. The probability of inducing fibrillation was increased by stimulating the heart with a short burst of high-frequency pacing before each measurement (arrow in FIG. 10b). Perfusion with 170 nM GsMtx-4 suppressed both the incidence (FIG. 10c) and duration (FIG. 10d) of fibrillation in all hearts (n=10). At pressures below 17.5 cm H$_2$O, sustained fibrillation was completely inhibited in all preparations (data not shown). GsMTX-4 did not block stretch-induced shortening of the refractory period.

The data presented in these Examples indicates that the peptide of the present invention blocks SACs in rat astrocytes, rabbit cardiac myocytes, and whole rabbit hearts in a stretch-dependant manner. Since stretch sensitivity is not unique to any particular chamber of the heart, GsMTx-4 can be used similarly on all chambers. This peptide should therefore be useful in elucidating the function of SACs in a variety of systems under physiologically normal and stressed conditions, and for blocking SACs associated with pathological conditions such as cardiac arrhythmias.

EXAMPLE 6

This embodiment describes the cloning of the cDNA for the GsMTx-4 peptide.

Isolation and Analysis of GsMTx4 cDNA

RNA Extraction Spider glands from tarantulas (*Grammostola spatulata*) were removed, flash frozen in liquid nitrogen, and stored at –80° C. (SpiderPharm). RNA extraction was done by homogenizing glands in Trizol. Approximately 55 µg of RNA were recovered from 3 glands. The quality of the RNA was determined according to previously published methods (Farrell, S. N., 1993). Each sample was applied to an agarose gel and analyzed with ferret liver RNA as a control. While the quality of the RNA was excellent, the 28S RNA was missing, a phenomenon associated with invertebrates where the 28S ribosome is specifically cleaved during isolation, resulting in a doublet that migrates with the 18S ribosome (Ishikawa, H, 1977).

cDNA Preparation Amplification was carried out using Clonetech's SMART RACE cDNA Amplification Kit and recommended procedures. The 5' and 3' RACE primer design were based on the GsMTx4 amino acid sequence and the codon frequency found in *Drosophila*, as no information is available on spider codon usage. The oligonucleotide sequences used are shown below:

5' RACE MTx 4-1: 5'-TCG TTG GGG TTG CAC TTC CAC CAG-3' (SEQ ID NO:5)

3' RACE MTx 4-1: 5'-TTC TGG TGG AAG TGC AAC CCC AAC G-3' (SEQ ID NO:6),

Criteria for primer sequences were based on minimizing variability for codon usage and the necessity for touchdown PCR (Clonetech manual). The latter requires a T$_m$ above 70° C., GC content close to 50–70%, and a primer length between 23 and 28 nucleotides.

Following the initial RACE reaction, 10 µl from each PCR was analyzed. A prominent band was observed from both the 5' and 3' RACE reactions (both slightly larger than 300 bp), with fainter background bands. The remaining product was purified, providing a template for a PCR reaction. Two sets of PCR primers were used, UPM primers (from the Clonetech RACE kit) and 5' and 3' RACE primers (shown below), to amplify the DNA and to reduce background contamination.

5' RACE MTx 4-2: 5'-GCC ATT GTT TCC AGT TCT AGA TCA-3' (SEQ ID NO:7)

3' RACE MTx 4-2: 5'-CGA CAA TGA AGA CAT CTG TGG TGT TCG-3' (SEQ ID NO:8)

Both PCR products, one corresponding to the N-terminus of the protein and the other to the C-terminus, were sequenced. Based on these data, new primers were designed to allow TOPO TA cloning (Invitrogen) and to determine the DNA sequence in the region of the original primers (see below).

TA-MTx4-1 For: 5'-TCT GCA GAA TCT CGG TTA GTT GTT GTT T-3' (SEQ ID NO:9)

TA-MTx4-1 Rev: 5'-TCG AGA AGT TTG GAT CTC CAC GTA TCC-3' (SEQ ID NO:10)

TA-MTx4-2 For: 5'-ATG AAG ACA TCT GTG GTG TTC GTC ATT G-3' (SEQ ID NO:1)

TA-MTx4-2 Rev: 5'-TTA CTT GCC GAA TGA AAA GTT ACA CAA C-3' (SEQ ID NO:12)

Cloning of the full length gene was achieved in two steps. Using the forward and reverse primers of TA-MTx4-1 reverse and forward primers, the full length clone was amplified. These primers were used because of their high stringency which reduces the background amplification. A second round of amplification using forward and reverse primers of TA-MTx4-2 that are closer to the 5' and 3' ends of the gene, was used to amplify the full length cDNA. The PCR reaction produced a single band that was cloned using the TOPO TA cloning kit (Invitrogen). Five clones were sequenced from both directions and they all had the same sequence (FIG. 11).

Synthesis and Folding of GsMTx4

Peptide Synthesis The protected peptide of GsMTx-4 was synthesized on an Applied Biosystems 433A peptide synthesizer using a Boc/Bzl protection strategy.

All the amino acids were incorporated by O-(7-azabenzotriazol-1-yl)-1,1,3,3-tetramethyluronium hexafluorophosphate (HATU) with p-methylbenzhydrylamine resin as the solid support. Side chain protecting groups employed were: 4-methylbenzyl for Cys, tosyl for Arg, 2-chlorobenzyloxycarbonyl for Lys, cyclohexyl for Asp and Glu, cyclohexyloxycarbonyl for Trp, and Bzl for Ser. Removal of protecting groups and cleavage from the resin were simultaneously accomplished by treatment of the resin with anhydrous hydrogen fluoride (HF) at −4∼−5° C. for 60 min in the presence of p-cresol and buthanedithiol (BDT) as scavengers (HF/p-cresol/BDT=85:10:5). Excess HF was evaporated, the cleaved product precipitated with ether, and the solid material collected by filtration. The crude reduced peptide was extracted with 0.1% TFA and purified by reversed phase-high performance liquid chromatography (RP-HPLC) on a YMC C-18 column (3.0×25 cm). A gradient elution of $CH_3CN$ in aqueous 0.1% trifluoroacetic acid (TFA) was used to elute the peptide.

Peptide folding The reduced peptide was collected, evaporated to dryness and dissolved in 0.1 M Tris-HCl at pH 7.8 to a concentration of $10^{-5}$ M. Reduced and oxidized gluthathione (GSH and GSSG, respectively) were added to the reaction mixture in a molar ratio of 1:100:10 (peptide: GSH:GSSG). After stirring for 24 h at room temperature, the reaction was terminated by the addition of TFA. The resulting solution was injected onto a YMC C-18 column, and the peptide was eluted by a linear gradient of $CH_3CN$ in aqueous 0.1% TFA. The pooled fractions of the product were re-purified using the same elution conditions. The peptide was passed through a Muromac column followed by a Sephadex LH-20 using 1% AcOH in both cases. The effluent was lyophilized to obtain an amorphous powder of synthetic GsMTx-4.

RP-HPLC analysis RP-HPLC analysis was run on a YMC C-18 column (4.6×150 mm) at a flow rate of 1.0 ml/min at 50° C. For monitoring the progress of the reaction and the purity of the product in each purification step, a linear gradient of $CH_3CN$ from 10% to 60% over 25 min in water containing 0.1% TFA was employed. For chromatographic comparison of synthetic GsMTx-4 with the natural peptide, similar conditions were used except that the concentration of $CH_3CN$ was from 27% to 37%. The chromatogram was monitored at 220 nm and 280 nm wavelengths.

Other analyses Matrix-assisted laser desorption/ionization time-of-flight mass spectrometry (MALDI-TOF MS) analysis was conducted on an Applied Biosystems Voyager-DE STR mass spectrometer at 20 kV using reflector mode. Electrospray ionization-mass spectrometry (ESI-MS) was performed on a HP1100LC/MSD mass spectrometer equipped with a YMC C-18 column in a liquid chromatography mode. Capillary zone electrophoresis (CZE) analysis was run on a Photal CAPI-3300 using 50 mM phosphate buffer at pH 2.5. UV detector was set at 200 nm.

Cloning of GsMTx4

Expression vector: The gene encoding ala-GsMtx4 (C-terminal alanine) was PCR amplified and cloned into a modified pGEM vector (a gift from M. Morales SUNY Buffalo). The forward PCR primer contained nucleotides that encoded a thrombin cleavage site as well as a KpnI restriction site: 5' GCACGTGGTACCCTGGTGCCA-CGCGGCTC-TATGGGCTGCCTGGAA 3' (SEQ ID NO:13). The reverse primer was designed to include the XhoI restriction: 5' GCACGCTCGAGCTACGCGCTGCTAAAG3' (SEQ ID NO:14). The amplification reaction was cycled as follows, 95° C. for 45 sec, 60° C. for 45 sec, and 72° C. 60 sec for 35 cycles. The PCR product was cleaved in the presence of XhoI and KpnI enzymes, purified by agarose gel, and extracted by a Qiagen column according to specified procedures. Subsequently, the PCR fragment was ligated into the KpnI/Xho I sites in the modified pGEM vector at 17° C. overnight and transformed into DH5α competent cells. Miniprep analysis was done using Qiagen columns. The resulting thioredoxin/alaGsMtx4 fusion gene was excised from the pGEM vector with XbaI and XhoI and cloned into the pET32a expression vector (Novagen, Madison Wis.) at the XbaI and XhoI sites following the above protocols.

Mutagenesis of the GsMtx4 gene: To convert ala-GsMtx4 to the wild type sequence, two sequential mutagenesis reactions were performed. Ten ng of pET32a/alaMTX4 vector was amplified in a site-directed mutagenesis reaction (Stratagene, La Jolla, Calif.). Primers that introduced the amino acid change were: S34F forward 5'CTGTGCAACTT-TAG-CTTCGCGTAGCTCGAGC3' (SEQ ID NO:15) and S34F reverse 5' GCTCGAGCTACGCGAAG-CTAAAGT-TGCACAG3' (SEQ ID NO:16). The reaction was incubated with 2.5 U of Pfu Turbo Taq Polymerase and cycled as follows, 95° C. for 30 sec, 55° C. for 1 min and 68° C. for 12 minutes for 16 cycles. The parental DNA was digested with 10 U of DpnI at 37° C. for 1 hour. The newly synthesized DNA was transformed into XL1-blue E. Coli.

To replace alanine 35 with a stop codon: 10 ng of the pET 32a/MTX4 (S34F) was amplified in a site-directed mutagenesis reaction. Alanine 35 was changed to a stop codon using the following primers: A35X forward 5' GCAACTT-TAGCTTC-TAGTAGCTCGAGCACCACC 3' (SEQ ID NO:17) and A35X reverse 5'CGTTGAAATCGAAG-AT-CATCGAGCTCGTGGTGG 3' (SEQ ID NO:18). The reaction was done as described above.

Protein Purification: The vector was introduced into BL21 (DE3) E. coli strain. An overnight culture of 100 mL was grown in the presence of carbenicillin (5 mg). This was added to a 10 L of L-Broth in a fermentor (New Brunswick) and conditions were maintained according to manufacturer's recommendation. Growth of the bacteria was followed by measuring the optical density (OD) at 600 nm. At an OD of 0.45, 3.3 grams of IPTG was added and allowed to incubate for an additional 2.5 hours.

The cells were harvested and lysed according to the following procedure.

After centrifugation, cells (1 Liter) were suspended in 20 mM Tris pH 7.9, 0.5M NaCl, and 5 mM imidazole (total volume of 200 mL). The suspension was frozen at −70° C. overnight. Cells were then thawed at 30° C. and 400 µl of lysozyme (10 mg/ml) was added and allowed to incubate at 30° C. for 5 min. To this mixture the following protease inhibitors were added: 500 µl of pepstatin (6 mg/ml), 500 µl of AEBSF (100 mg/ml), 500 µl 1 E64(3.6 mg/mL), and 125 phosphoramidon (5.4 mg/ml). βmercaptoethanol was added (70 µl), and the entire solution was mixed by inversion. The cell suspension was divided into two portions (~100 mL) and each was sonicated 3 times at full power for 1 minute at 4° C. Insoluble material was collected by centrifugation ($1^{st}$ pellet). The soluble fraction was heated to 60° C. for 10 minutes causing protein to precipitate which was collected by centrifugation ($2^{nd}$ pellet). All 3 fractions, ($1^{st}$ pellet, $2^{nd}$ pellet and soluble fraction) were analyzed by SDS-PAG electrophoresis and the majority of the fusion protein was shown to be in the $1^{st}$ pellet. This pellet was dissolved by in 10 ml of binding buffer (20 mM Tris-HCl pH 7.9, 0.5 M NaCl, 5 mM imidazole) with 6M guanidine HCl and heated to 30° C. for 30 minutes. The remaining insoluble material was removed by centrifugation. The resulting soluble fraction was collected and the fusion protein was purified on a HiTRAP column.

Purification by Ni-NTA Five ml of Ni-NTA resin (Qiagen) was prepared according manufacturer's specification. The resin was then equilibrated with binding buffer. Approximately half of the extract (5 ml) was loaded onto the Ni-NTA column using binding buffer in the presence of 6M guanidiniumHCl. The fusion protein was desorbed by a stepwise gradient of imidazole (20 mM, 100 mM and 500 mM) in a buffer (20 mM Tris-Hcl pH 7.9, 0.5 M NaCl and 6M guanidine HCl). Protein that eluted with the highest imidazole concentration (500 mM) was collected and solid DTT was added to a final concentration of 0.1M. After 30 min incubation the solution was acidified with acetic acid to pH ~4.5 and dialyzed against 20 mM Tris-HCl pH 6.5.

GsMTx4 from fusion protein Fusion protein was dialyzed with 0.1M Tris-HCl pH 7.9 and 0.5M guanidiniumHCl. Folding was achieved by the addition of 0.1 mM of oxidized gluthathione and 1 mM reduced gluthathione and adjusting the protein concentration to $10^{-5}$M. The reaction was completed after 24 hours at rt. Thrombin cleavage was acheived by adding 10× cleavage buffer (1/10 volume) to the folding reaction and adding 1 unit of thrombin per 1.5 mg of fusion protein. The reaction was followed to completion by RP-HPLC.

Circular Dichroism

Peptide was dissolved in 5 mM phosphate buffer pH 6.9 at indicated concentrations (0.5–80 µM). Spectra were collected on a Jasco 710 under a constant stream of nitrogen at a rate of 0.2 nm/sec. The path length for the cell was 0.1 cm for the high concentrations of peptide and 1 cm for low concentrations. Each experiment was an average of four readings. Background spectra were measured in the absence of peptide and were subtracted from the peptide spectra.

Structural Determination by NMR

NMR Spectroscopy: A 1 mg sample of synthetic GsMTx4 was dissolved in 250 µl of distilled $H_2O$ (final concentration of 3.9 mM). The samples were then titrated to approximately pH 4.5 and $D_2O$ was added to 8%. The entire protein solution was transferred to a 5 mm Shigemi tube for NMR spectroscopy. All experiments were performed on Varian Inova 500 Spectrometer equipped with triple resonance gradient probes at the Cornell Biomolecular NMR Center. Data were collected in States-TPPI mode (Kanzaki, M. et al., 1999) for quadrature detection. Homonuclear 2D NOESY (Kumar, A. et al., 1980), TOCSY(Caravatti, P. et al., 1983), and COSY (Aue, W. P. et al., 1976) spectra were obtained at 15° C., 25° C., and 37° C. with presaturation during the recycle period followed by SCUBA recovery (Brown, S. C. et al., 1988). A DIPSI-2 (Rucker, S. P. and SHAKA, A. J., 1989) sequence of 60 ms was used in the TOCSY experiments, and a 150 ms mixing period was used in the NOESY experiments. 2D [$^1$H,$^{15}$N]HSQC and [$^1$H, $^{13}$C]HSQC (Bodenhausen, G & Ruben D J, 1980) spectra were acquired with natural abundance proteins. Data were processed either with NMRPipe (Delaglio, F. et al., 1995), and Sparky (Goddard, T. D. and Kneller, D. G., 2001) was used for data visualization, assignments, and peak integration. Dihedral angle constraints were obtained from the chemical shift index (csi) (Wishart, D. S. and Sykes, B. D., 1994;Wishart, D. S. et al., 1992;Wishart, D. S. et al., 1991) using chemical shifts from $C^\alpha$, $C^\beta$, and $H^\alpha$.

Structure calculation Distance constraints for structural calculations were obtained from a series of 2D homonuclear NOESY experiments at 5 to 35° C. in either 90% $H_2O$/10% $D_2O$ or 100% $D_2O$. Distance constraints were classified into four categories according to the intensity of the NOE crosspeak (<2.4, <3.4, <4.0, and <5.5 Å). On the basis of the csi, backbone dihedral angles were constrained to favorable regions of φ, ψ space: α-helix, φ, −80±30°; ψ−20±30°; β-strand, φ, −105 ±65°; ψ, 145±45°. The distance and dihedral restraints were used as inputs to determine preliminary structures using the distance geometry/simulated annealing protocol in CNS 1.1 (Crystallography and NMR System; (Brunger, A. T. et al., 1998). Three hundred structures were calculated using CNS and the twenty lowest energy structures were aligned to the average structure using XPLOR 3.851 (Brunger, A. T., 1996). The structures were visualized using Swiss-PdbView (Guex, N. and Peitsch, M. C., 1997) and analyzed using Procheck-NMR, Aqua (Laskowski, R. A. et al., 1996), and NMRCLUST (Kelley, L. A. et al., 1996).

Patch Clamp Assay

NRK cell culture: Normal rat kidney cells (CCA identifier is 49F) at passages 20–25, were maintained in DMEM, 5% fetal bovine serum and 1%

Penicillin/Streptomycin. Cells were plated onto poly-L-lysine coated cover-slips, and used in experiments between 2 and 6 days after passage.

Electrophysiology: An Axopatch 200B (Axon Instruments, California) was used for patch clamping, while experimental protocols and data acquisition were controlled by Axon Instruments pClamp8 software via a Digidata 1322A acquisition system. Currents were sampled at 10 KHz and low-pass filtered at 2 KHz through the 4 pole Bessel filter on the Axopatch 200B. All potentials are defined with respect to the extracellular surface. Electrodes were pulled on a Model PC-84 pipette puller (Brown-Flaming Instruments, California), painted with Sylgard 184 (Dow Corning Corp. Midland Mich.) and fire polished. Electrodes were filled with KCl saline (KCl 140 mM, EGTA 5 mM, $MgSO_4$ 2 mM, Hepes 10 mM, pH 7.3) and had resistances ranging from 10–20 MΩ. Bath saline consisted of NaCl—140 mM, KCl—5 mM, CaCl$_2$—2 mM, MgSO$_4$—0.5 mM, glucose—6 mM and Hepes—10 mM, pH 7.3. Pressure and suction were applied to the pipette by a HSPC-1 pressure clamp (ALA Scientific Instruments, New York) controlled by the pClamp software. Perfusion of toxin samples was performed by a pressurized local perfusion system BPS-8 (ALA scientific instruments, NY) with 8 separate channels. Off-line data analysis was performed with Clampfit and Origin 6.1 software.

Results

We have sequenced the cDNA of GsMTx4 isolated from the glands of *Grammostola spatulata*. Translation of the cDNA indicated that the peptide GsMTx4 is made as a preproform (see FIG. 11) and undergoes post-translational processing to achieve the mature form. The first 21 amino acids (FIG. 11—bold letters) are predicted to be a signal sequence and are probably removed during protein translocation (Nielsen, H. et al., 1997). The last two amino acids are glycine-lysine (FIG. 11—bold and italicized letters), a known processing site for amidation (Devaux, C. et al., 1995); (Bradbury, A. F. and Smyth, D. G., 1991;Zabriskie, T. M. et al., 1994). An arginine adjacent to the active toxin molecule is presumably the cleavage site for active GsMTx4 (FIG. 11—arrow) from the pro region (shaded box). The overall design of this protein is similar to other precursor toxins that undergo processing. Most notable is the O-super family of conotoxins that are translated in a preproform, specifically the α conotoxin (Woodward, S. R. et al., 1990; Lewis, R. J. et al., 2000;Olivera, B. M. et al., 1991;Olivera, B. M. et al., 1990;Colledge, C. J. et al., 1992). Preproconotoxins have a 21 amino acid signal for translocation, have in many instances amidation sites at the C-terminus, and are cleaved after an arginine to release the mature peptide. Interestingly, conotoxin cDNAs isolated from the venomous gastropod Conus display a diverse array of peptides for a given species (Duda Jr., T. F. and Palubi, S. R., 2000;Duda, T. F., Jr. and Palumbi, S. R., 1999). We have found only a single cDNA sequence for GsMTx4 from the 3 glands of GS that we isolated.

Figure 12:
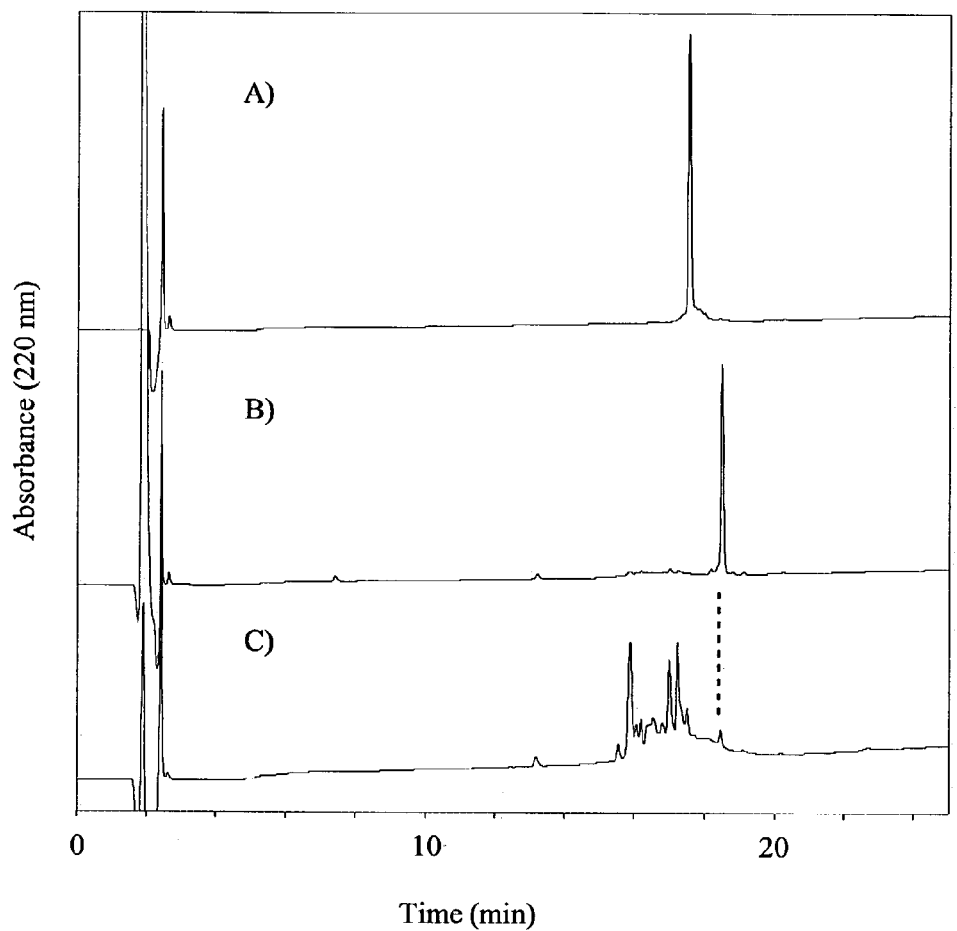
FIG. 12 shows oxidative folding reaction of synthetic GsMTx-4. A) Reduced and unfolded synthetic GsMTx-4. B) Folded and Oxidized peptide in the presence of GSH/GSSG. C) Folded and oxidized peptide in the absence of GSH/GSSG. RP-HPLC analysis was achieved with a linear gradient of 10%–60% $CH_3CN$ in 0.1% TFA (25 min) and monitored at 220 nm.

Based on the sequence from the cDNA and assuming the peptide was amidated at the C-terminus, we chemically synthesized GsMTx4 with a C-terminal phenylalanine and not a serine-alanine as originally described (Suchyna, T. M. et al., 2000). The reduced synthetic peptide was subjected to the oxidative folding reaction in the presence of GSH/GSSG. A comparison of FIGS. 12A and 12B shows that the correctly folded structure has a longer retention time in comparison to the unfolded peptide. This indicates that GsMTx4 is more hydrophobic in the folded state.

Figure 13:
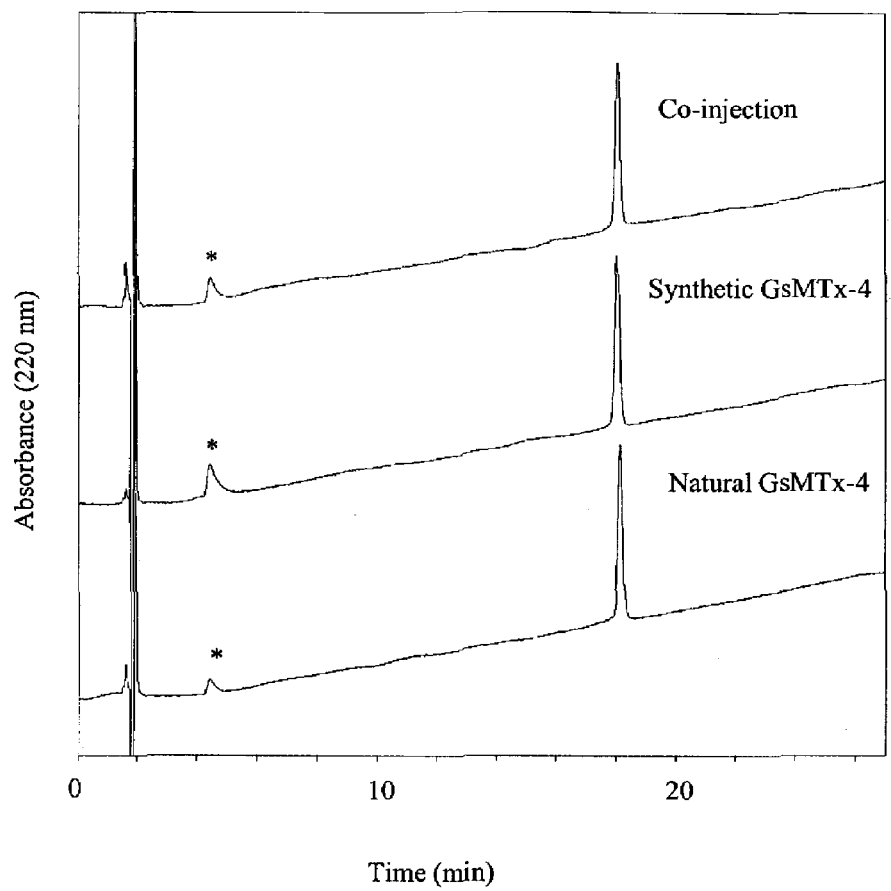
FIG. 13 shows a comparison of retention times by RP-HPLC of wild type and synthetic GsMTx4 peptide. Synthetic and wild type peptides were injected separately (bottom panels) and then combined and injected (top panel). A gradient between 27%–37% $CH_3CN$ in 0.1% TFA (25 min) was used and monitored at 220 nm. The peak at 4.5 min (indicated by asterisks) is not peptide material as there is no absorbance at 280 nm.

We compared the properties of the synthetic and wild type peptides, to confirm that the synthetic peptide was folded correctly. Co-injection of both peptides on RP-HPLC (FIG. 13) showed that the wild type and synthetic GsMTx4 co-eluted as a single peak. We altered the conditions to isocratic at 31.5% CH$_3$CN concentration in 0.1% TFA and obtained the same (t=10.8 min, data not shown). Furthermore, we found that in the CZE analysis, both synthetic and natural peptides co-migrated with identical retention time of 14.7 min. Molecular weight (MW) of the product was measured by MALDI-TOF MS [M+H$^+$4093.9, monoisotopic], showing that the three intramolecular disulfide bonds had formed to generate the monomeric peptide.

We were interested in the thermodynamic stability of the peptide and the role of disulfide formation on achieving the lowest energy folded state. In the absence of GSH/GSSG (FIG. 12C) we observed only a minor fraction of peptide that was folded correctly. The majority of the peptide had faster retention times and multiple peaks that represented misfolded populations, most of them having the identical MW to the native structure. A mixture of GSH/GSSG was then added to the reaction mixture whose HPLC trace is shown in FIG. 12C and the population of peptide shifted to the correctly folded state that was easily detected by RP-HPLC (FIG. 12B). Clearly a major barrier to the correctly folded peptide is the formation of incorrectly paired disulfides.

Figure 14:
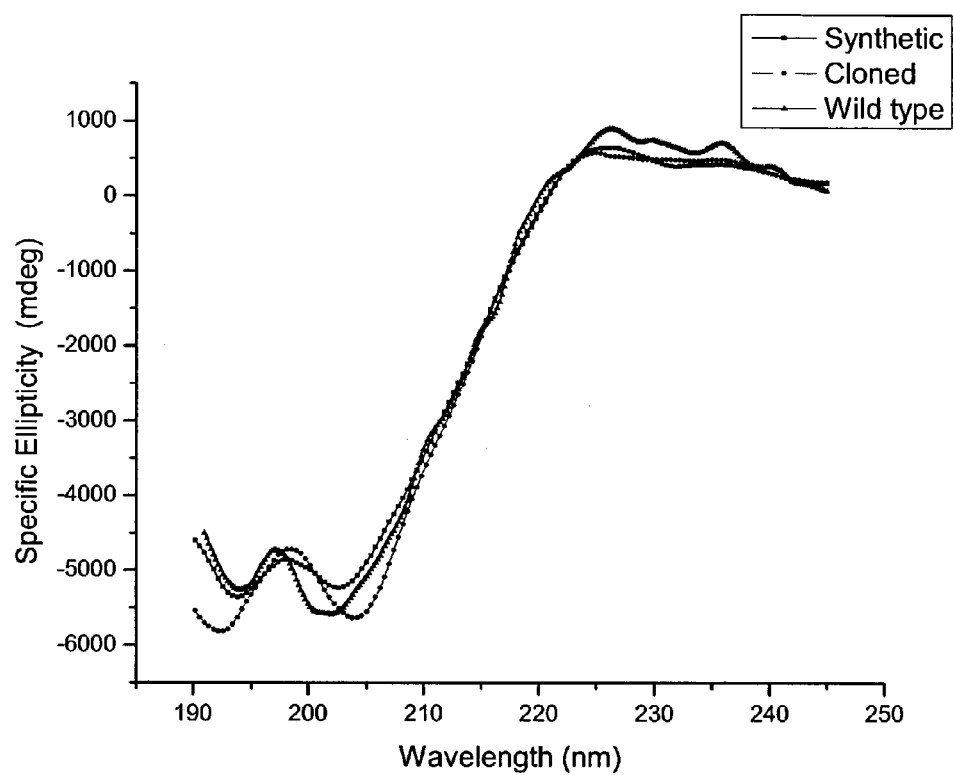
FIG. 14 shows Circular Dichroism measurements of GsMTx4 peptides. Each Peptide was dissolved in 5 mM Phosphate buffer at pH 6.9 and analyzed. Baseline was determined by measuring the phosphate buffer in the absence of peptide and was subtracted from all spectra.

The structure of synthetic and wild type peptide using Circular Dichroism and NMR spectroscopy was analyzed. Circular Dichroism spectra for both peptides are generally the same (FIG. 14), as both have minima at around 192 and 202 nm. An analysis of the peptide spectra using the program CONTIN indicated that they both have a similar content of beta turns and beta strands (Provencher, S. W. and Glockner, J., 1981;van Stokkum, I. H. et al., 1990). No helical structure is predicted and the minimum at 202 nm is normally associated with unstructured peptide. The meaning of the CD spectrum is not entirely clear as the NMR structure is a compact and generally organized molecule. We have observed no significant differences in CD spectra for the naturally occurring GsMTx4 peptide when measured over a range of concentrations (500 nM–80 µM) indicating that the peptide does not have higher order interactions. These results are similar to the NMR analysis of GsMTx4 in which the diffusion constant (D$_r$) was consistent with a monomeric species (Oswald, R. E. et al., 2002).

We note that there are some differences between the two peptides in the far UV region at the 192 minima, 202 nm, and in the near UV region (220–230 nm) as well as for the cloned peptide discussed below. The spectral minima observed around 192 nm with contributions at 220–230 nm are usually associated with the type I □-turn. The reason for these spectral differences is not immediately evident but it may reflect subtle conformational changes that are dependent on small changes in pH for example. The NMR data described below are consistent with this assessment since the overall structures of peptides were not significantly different in beta strand orientation (see FIG. 16). A more thorough investigation of peptide CD spectra as a function of pH is currently underway. These measurements will be correlated with NMR data of $^{15}$N enriched peptide that allow for a higher resolution structure with a more accurate assessment of dynamic properties of the backbone.

Figure 15:
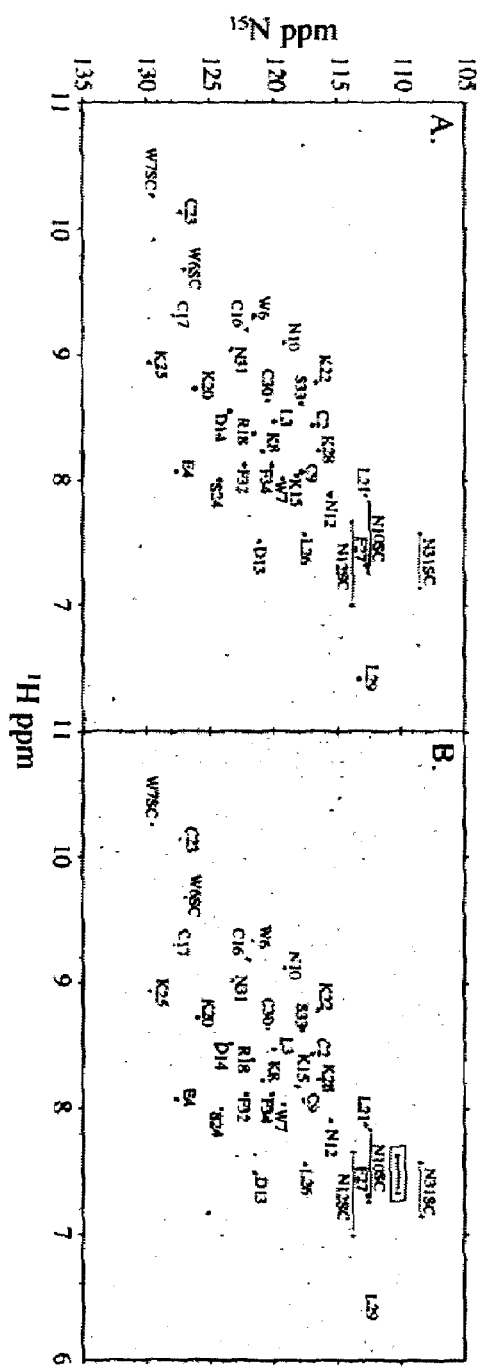
FIG. 15 shows the natural abundance $^1$H, $^{15}$N spectra of GsMTx4 wild type (Panel A) and synthetic (Panel B) peptides. Data were collected at 600 MHz, averaging 512 transients at each of 128 increments. All backbone N—NH correlations were observed except for the N-termini.
Figure 16:
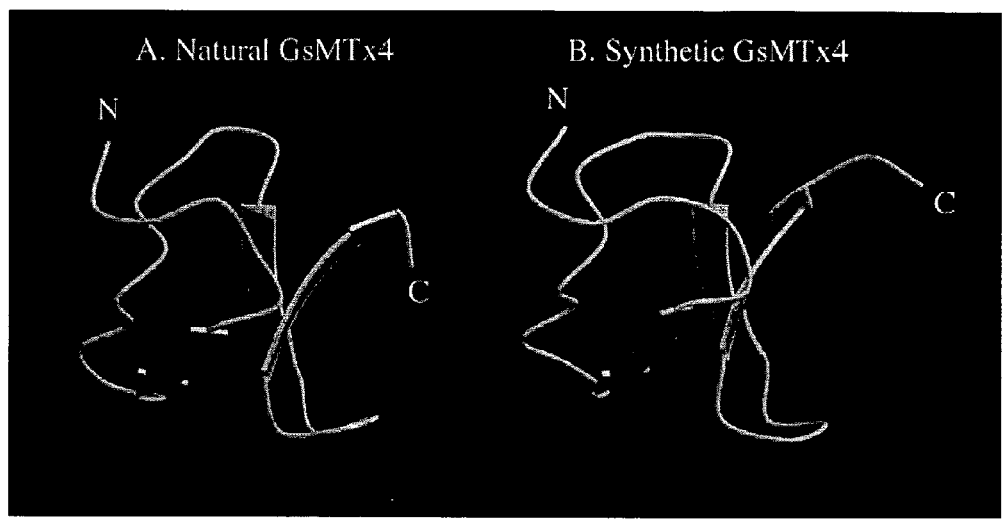
FIG. 16 shows three dimensional structures of GsMTx4 wild type and synthetic peptides. The most representative structure from each peptide is shown with the secondary structure indicated.

NMR spectra obtained from the synthetic version were nearly identical to data obtained from natural GsMTx4 purified from the venom of *Grammostola spatulata*. Minor variations that we have observed are attributable to small differences in pH. This is evident from the comparison of the $^1$H, $^{15}$N—HSQC spectra shown in FIG. 15. Likewise the NOESY, TOCSY and double quantum filtered COSY spectra were virtually identical. Using only the distance constraints from the NOESY spectra collected in 90% H$_2$O/10% D$_2$O and the coupling constants inferred from the chemical shift index based on the TOCSY and $^1$H,$^{13}$C-HSQC, experiment preliminary structures were calculated using CNS 1.1. Representative structures from the set of 20 lowest energy structures from both purified GsMTx4 and synthetic GsMTx4 are shown in FIG. 16. The backbone folds were identical for the two versions of the protein.

We have cloned this peptide as part of a thioredoxin fusion protein. We used a vector that has 6 histidines and a thrombin cut site 3 amino acids away from the multiple cloning region where the gene for GsMTx4 was inserted. We were forced to position the endoproteolytic cut site distal to the N-terminus because we were unable to cleave GsMTx4 from the fusion when it was adjacent to N-terminus. The fusion protein does have a methionine next to the N-terminus and, because there are no methionines in GsMTx4, we are able to cleave the peptide with cyanogens bromide (data not shown) to generate folded GsMTx4 that has a free carboxyl group.

Figure 17:
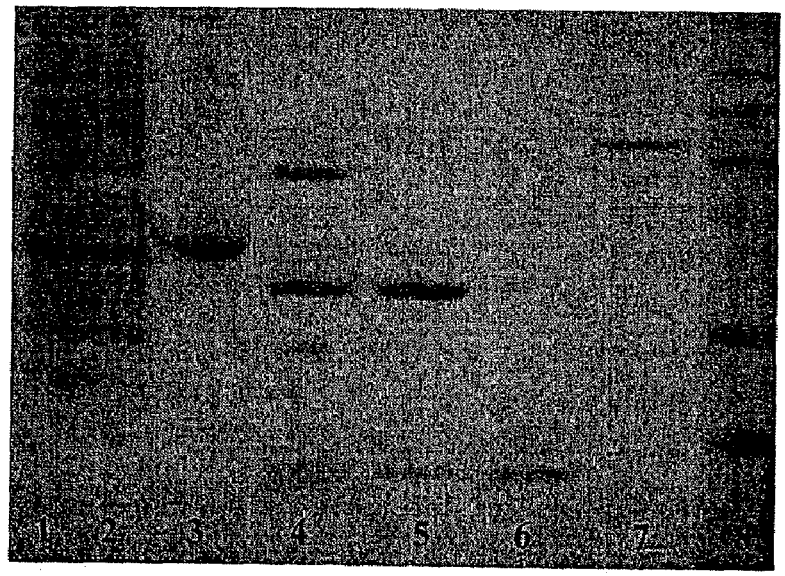
FIG. 17 shows a visualization of the thrombin cleavage reaction by 12% SDS-PAG electrophoresis. Lanes 1 and 2 are crude fractions at 2 different concentrations. Lane 3 is purified fusion protein after induction. Lanes 4 and 5 are thrombin cleavage reactions at two different thrombin concentrations, 3.8 and 0.4 units respectively. Lane 6 is wild type GsMTx4 purified from *Grammostola spatulata*. Lane 7 is the control protein incubated with thrombin. Lane 8 is protein markers.
Figure 18:
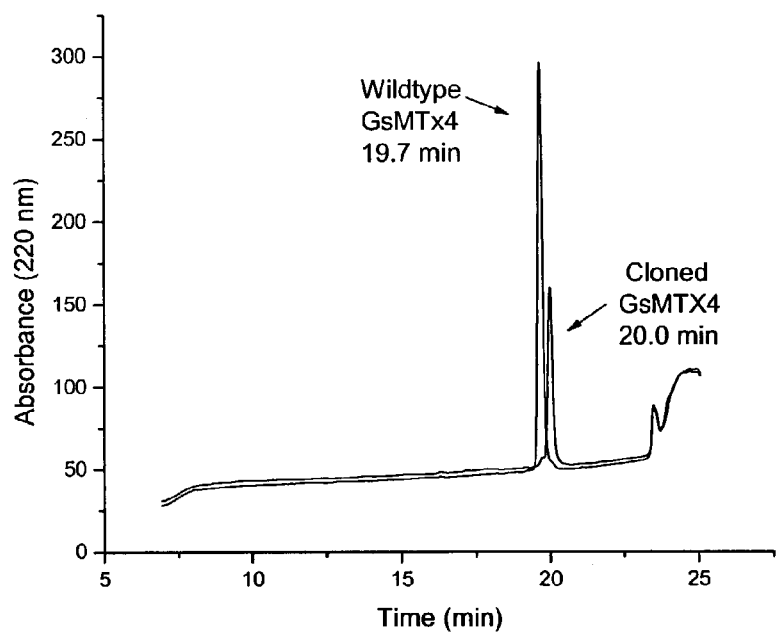
FIG. 18 shows a comparison of retention times by RP-HPLC of wild type (3 µg) and cloned (1.4 µg) GsMTx-4 peptide. A gradient between 20%–48% CH$_3$CN in 0.1% TFA (25 min) was used and was monitored at 220 and 280 nm. The difference in migration is due to the extra amino acids (Ser-Gly-Met) at the N-terminus.

IPTG induction of the protein in *E. coli* resulted in a completely insoluble protein fraction. Because nickel affinity columns are stable in denaturants, a two step chromatographic process was developed that produces ~300 μg of peptide from a liter culture of cells. The fusion protein was first dissolved by the addition of 6 M guanidiniumHCl and then purified on an affinity column (see Lanes 2 and 3, FIG. 17). The peptide was folded using similar conditions to those described above for the synthetic peptide, but 0.5M guanidiniumHCl was added to help maintain solubility. Thrombin cleavage overnight at room temperature quantitatively liberates the peptide from the fusion protein (compare Lanes 5 and 6 in FIG. 17). High concentrations of thrombin tend to lead to secondary cleavage reactions (Lane 4, FIG. 17). The resulting peptide has an extra 3 amino acids and is retained slightly longer (30 sec) than the wild type peptide (see FIG. 18) having a mass of 4370.33 [MH$^+$]. The CD spectrum of the peptide is qualitatively similar to wild type and synthetic peptides with the distinction of having a larger contribution to the spectrum around 192 nm peak (see FIG. 14). The NMR spectrum showed that the NOE signals are similar to that of wild type (data not shown).

Figure 19:
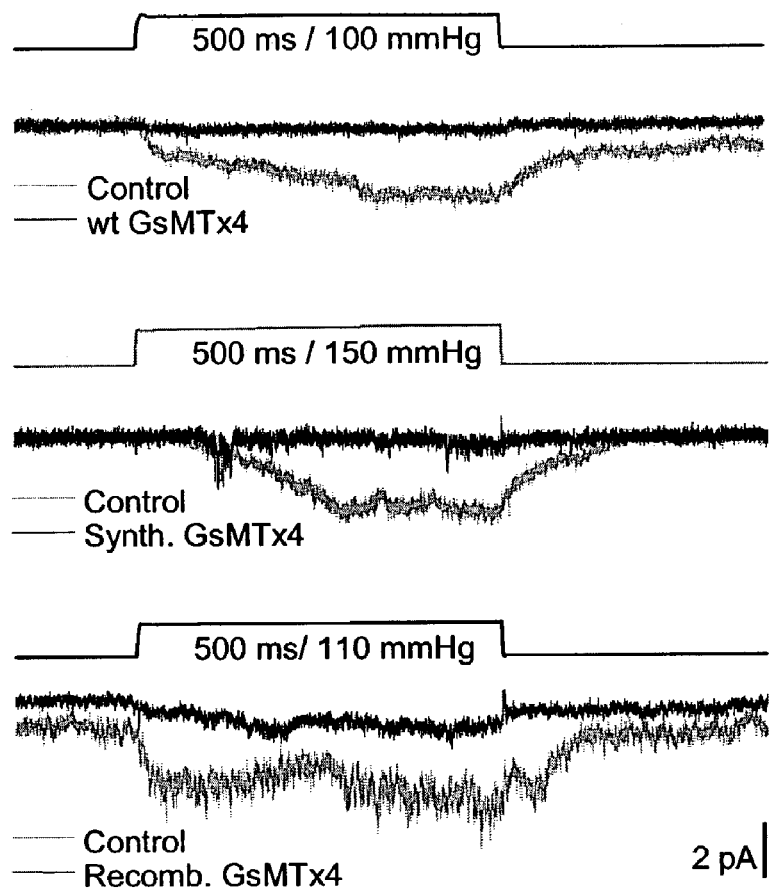
FIG. 19 shows wild type, synthetic, and recombinant forms of GsMTx4 block MSC currents in normal rat kidney cells. Peptides were applied to outside-out patches held at −50 mV, and the average patch currents were calculated from 15–20 pressure steps before (control—gray traces) and during (black traces) application of the three peptide forms. At 5 µM concentration, each peptide blocked >90% of the mechanically sensitive current.

Both the synthetic and cloned peptide were tested for their ability to inhibit mechanosensitive channels on kidney cells (FIG. 19). Using either the cloned or synthetic peptide at 5 μM, the mechanosensitive channels of kidney cells were blocked. Interestingly, the presence of the extra amino acids at the N-terminus and the lack of amidation did not significantly affect the activity (greater than 75% block). The N-terminus appears to be a useful site for introducing a fluorescent or spin label for biophysical studies. This contrasts with observations made for apamin (Devaux, C. et al., 1995) where the absence of C-terminal amide reduced activity and was accompanied by a significant perturbation to the peptide structure as determined by CD spectra.

The foregoing description of the specific embodiments is for the purpose of illustration and is not to be construed as restrictive. From the teachings of the present invention, those skilled in the art will recognize that various modifications and changes may be made without departing from the spirit of the invention.

---

We claim:

1. An isolated and purified peptide comprising the sequence selected from the group consisting of SEQ ID NO:1, SEQ ID NO:2 and SEQ ID NO:3.

2. The isolated peptide of claim 1, wherein the peptide has the sequence of SEQ ID NO:1.

3. The isolated peptide of claim 1, wherein the peptide has the sequence of SEQ ID NO:2.

4. The isolated peptide of claim 1, wherein the variant peptide has the sequence of SEQ ID NO:3.

5. The peptide of claim 1, wherein the peptide is a synthetic peptide.

6. The peptide of claim 1, wherein the peptide is a recombinant peptide.

7. A pharmaceutical composition comprising the peptide of claim 1 in a pharmaceutically acceptable carrier or diluent.

8. The pharmaceutical composition of claim 7, wherein the peptide has the sequence of SEQ ID NO:2.

9. A method of reducing cardiac arrhythmia comprising administering the peptide of claim 1 in a pharmaceutically acceptable carrier in an amount effective to reduce cardiac arrhythmia to a patient in need of treatment.

10. The method of claim 9, wherein the peptide has a sequence of SEQ ID NO:2.

11. A method of blocking stretch-activated channels in a cell comprising the step of contacting the cell with a sufficient amount of the peptide of claim 1 effective for blocking stretch activated channels in the cell.

12. The method of claim 11, wherein the cell is a myocardial cell.

13. The method of claim 11, wherein the cell is an astrocyte.

14. The method of claim 11, wherein the peptide is used for blocking stretch activated channels during catheterization.

* * * * *

UNITED STATES PATENT AND TRADEMARK OFFICE
CERTIFICATE OF CORRECTION

| | |
|---|---|
| PATENT NO. | : 7,125,847 B1 |
| APPLICATION NO. | : 10/397595 |
| DATED | : October 24, 2006 |
| INVENTOR(S) | : Sachs et al. |

It is certified that error appears in the above-identified patent and that said Letters Patent is hereby corrected as shown below:

Column 1 – line 12, insert:

--This invention was made with Government support under Grant
No. 5R01HL5488705 awarded by the National Institutes of Health.
The Government has certain rights in the invention--.

Signed and Sealed this

Ninth Day of June, 2009

JOHN DOLL
*Acting Director of the United States Patent and Trademark Office*